US012163957B2

(12) United States Patent
Raducanu et al.

(10) Patent No.: US 12,163,957 B2
(45) Date of Patent: Dec. 10, 2024

(54) METHODS FOR DETECTING HIS-TAGGED PROTEINS USING NTA PROBES AND POLYACRYLAMIDE GEL ELECTROPHORESIS

(71) Applicant: King Abdullah University of Science and Technology, Thuwal (SA)

(72) Inventors: Vlad-Stefan Raducanu, Thuwal (SA); Ioannis Isaioglou, Thuwal (SA); Jasmeen S. Merzaban, Thuwal (SA); Samir M. Hamdan, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 325 days.

(21) Appl. No.: 17/332,254

(22) Filed: May 27, 2021

(65) Prior Publication Data

US 2021/0373012 A1  Dec. 2, 2021

Related U.S. Application Data

(60) Provisional application No. 63/032,914, filed on Jun. 1, 2020.

(51) Int. Cl.
*G01N 33/561* (2006.01)
*G01N 21/64* (2006.01)

(52) U.S. Cl.
CPC ....... *G01N 33/561* (2013.01); *G01N 21/6428* (2013.01); *G01N 2021/6439* (2013.01)

(58) Field of Classification Search
CPC ............ G01N 33/561; G01N 21/6428; G01N 2021/6439
See application file for complete search history.

(56) References Cited

U.S. PATENT DOCUMENTS

| | | | |
|---|---|---|---|
| 4,481,094 A | 11/1984 | Fernandez de Castro | |
| 5,656,145 A | 8/1997 | Nguyen | |
| 5,700,638 A * | 12/1997 | Korsmeyer | ............. A61P 35/00 435/7.1 |
| 6,878,257 B2 | 4/2005 | Manusu | |
| 2003/0141190 A1 | 7/2003 | Alpenfels | |
| 2007/0187252 A1 | 8/2007 | Alpenfels | |
| 2015/0275277 A1 * | 10/2015 | Cheng | .................. C12Q 1/6886 435/6.12 |
| 2020/0164104 A1 * | 5/2020 | Sawadkar | ........... A61L 27/3683 |

OTHER PUBLICATIONS

Vilber (Vilber 2015 Fusion FX Imaging System Product Introduction). (Year: 2015).*
Andersen, et al., "Optimized *E. coli* expression strain LOBSTR eliminates common contaminants from His-tag purification", Proteins, 81:1857-1861 (2013).
Bartoschik, et al. "Near-native, site-specific and purification-free protein labeling for quantitative protein interaction analysis by MicroScale Thermophoresis", Sci. Rep., 8:4977 (2018).
Bolanos-Garcia, et al., "Structural analysis and classification of native proteins from *E. coli* commonly co-purified by immobilised metal affinity chromatography", Biochim. Biophys. Acta., 1760(9):1304-1313 (2006).
Bornhorst, et al., "Purification of proteins using polyhistidine affinity tags", Methods Enzymol., 326:245-254 (2000).
Braner, et al., "Traceless' tracing of proteins—high-affinity trans-splicing directed by a minimal interaction pair", Chem. Sci., 7:2646-2652 (2016).
Bruchert, et al., "Ultrafast in-gel detection by fluorescent super-chelator probes with HisQuick-PAGE", Commun. Biol., 3:138 (2020).
Cooper, et al., "Cy3B: improving the performance of cyanine dyes", J. of Fluorescence, 14:145-150 (2004).
Gatterdam, et al., "Super-Chelators for Advanced Protein Labeling in Living Cells", Angewandte Chemie (International ed. in English), 57(20): 5620-5625 (2018a).
Gatterdam, et al., "The Scaffold Design of Trivalent Chelator Heads Dictates Affinity and Stability for Labeling His-tagged Proteins in vitro and in Cells", Angewandte Chemie (International ed. in English), 57(38):12395-12399 (2018b).
Grushka, "Characterization of exponentially modified Gaussian peaks in chromatography", Anal. Chem., 44(11):1733-1738 (1972).
Guignet, et al., "Reversible site-selective labeling of membrane proteins in live cells", Nat. Biotechnol., 22(4):440-444 (2004).
Holmes, et al., "Fluorescence quenching by metal ions in lipid bilayers", Biophys. Chem., 48(2): 193-204 (1993).
Huang, et al., "Tris-nitrilotriacetic acids of sub-nanomolar affinity toward hexahistidine tagged molecules", Bioconjug. Chem., 20:1667-1672 (2009).

(Continued)

*Primary Examiner* — Changhwa J Cheu
(74) *Attorney, Agent, or Firm* — PABST PATENT GROUP LLP

(57) ABSTRACT

Methods for detecting His-tagged proteins using metal ion-chelating nitrilotriacetate (NTA) probes and polyacrylamide gel electrophoresis (PAGE) are disclosed. In one embodiment, the method includes using a metal ion-loaded NTA probe coupled to a UV-excitable fluorophore with visible emission and the presence of His-tagged proteins in the sample is determined by exposing the gel following PAGE, to a UV-light source with naked human eye or bench camera visualization. The metal ion-loaded NTA-containing chelator head can be coupled to a fluorophore that is not UV-excitable (i.e., with the majority of emission and excitation in the visible region of the electromagnetic spectrum. The method includes separating proteins in a sample using PAGE, contacting the gel following electrophoresis with a composition containing a metal ion-loaded NTA probe coupled to the fluorophore, to allow binding of the probe to the His-tagged proteins, and detecting the presence of the probe and therefore of the His-tagged proteins.

18 Claims, 8 Drawing Sheets

(56) References Cited

OTHER PUBLICATIONS

Huang, et al., "Facile synthesis of multivalent nitrilotriacetic acid (NTA) and NTA conjugates for analytical and drug delivery applications", Bioconjug. Chem., 17(6):1592-1600 (2006).
Kalambet, et al., "Reconstruction of chromatographic peaks using the exponentially modified Gaussian function", J. Chemometr., 25:352-356 (2011).
Lai, et al., "Rapid labeling of intracellular His-tagged proteins in living cells", PNAS, 112(10):2948-2953 (2015).
Lata, et al., "Stable and functional immobilization of histidine tagged proteins via multivalent chelator headgroups on a molecular poly (ethylene glycol) brush", Anal. Chem., 77:1096-1105 (2005a).
Lata, et al., "Specific and stable fluorescence labeling of histidine-tagged proteins for dissecting multi-protein complex formation", Journal of the American Chemical Society, 128(7): 2365-2372 (2006).
Lata, et al., "High-affinity adaptors for switchable recognition of histidine-tagged proteins", Journal of the American Chemical Society, 127(29):10205-10215 (2005b).
Nothwang, et al., "Two-dimensional separation of membrane proteins by 16 BAC-SDS-PAGE", Methods in Molecular Biology, 528:269-77 (2009).
Piatkevich, et al., "Guide to red fluorescent proteins and biosensors for flow cytometry", Methods Cell Biol., 102:431-461 (2011).
Raducanu, et al., "A direct fluorescent signal transducer embedded in a DNA aptamer paves the way for versatile metal-ion detection", Sensor Actuat. B-Chem., 304:127376 (2020a).
Raducanu, et al., "Two chromatographic schemes for protein purification involving the biotin/avidin interaction under native conditions", J. Chromatogr. A, 1621:461051 (2020b).
Rashid, et al., "Initial state of DNA-Dye complex sets the stage for protein induced fluorescence modulation", Nat. Commun., 10(1):2104 (2019).
Roof, et al., "slyD, a host gene required for phi X174 lysis, is related to the FK506-binding protein family of peptidyl-prolyl cis-trans-isomerases", J. Biol. Chem., 269(4):2902-2910 (1994).
Taylor, et al., "Anionic lipid-induced conformational changes in human phagocyte flavocytochrome b precede assembly and activation 5 of the NADPH oxidase complex", Arch. Biochem. Biophys., 521(1-2):24-31 (2012).
Tehseen, et al., "Proliferating cell nuclear antigen-agarose column: A tag-free and tag-dependent tool for protein purification affinity chromatography", J. Chromatogr. A, 1602:341-349 (2019).
Valiokas, et al., Self-assembled monolayers containing terminal mono-, bis-, and tris-nitrilotriacetic acid groups: characterization and application, Langmuir, 24:4959-4967 (2008).
Van Broekhoven, et al., "The novel chelator lipid 3(nitrilotriacetic acid)-ditetradecylamine (NTA(3)-DTDA) promotes stable binding of His-tagged proteins to liposomal membranes: potent anti-tumor responses induced by simultaneously targeting antigen, cytokine and costimulatory signals to T cells", Biochim. Biophys. Acta., 1716: 104-116 (2005).
Wieneke, et al., "Multivalent Chelators for In Vivo Protein Labeling", Angewandte Chemie (International ed. in English), 58(25):8278-8290 (2019).
Williams, et al., "Structure and function of both domains of ArnA, a dual function decarboxylase and a formyltransferase, involved in 4-amino-4-deoxy-L-arabinose biosynthesis", J. Biol. Chem., 280(24):23000-23008 (2005).
Wulfing, et al., "An *Escherichia coli* protein consisting of a domain homologous to FK506-binding proteins (FKBP) and a new metal binding motif", J. Biol. Chem., 269(4):2895-2901 (1994).
Young, et al., "Recombinant protein expression and purification: a comprehensive review of affinity tags and microbial applications", Biotechnol. J., 7:620-634 (2012).

* cited by examiner

As visible to the naked eye

As imaged with gel-dock camera

METHODS FOR DETECTING HIS-TAGGED PROTEINS USING NTA PROBES AND POLYACRYLAMIDE GEL ELECTROPHORESIS

CROSS-REFERENCE TO RELATED APPLICATIONS

This application claims the benefit of and priority to U.S. Application No. 63/032,914, filed on Jun. 1, 2020, which is hereby incorporated herein by reference in its entirety.

FIELD OF THE INVENTION

This invention is generally in the field of protein detection.

BACKGROUND OF THE INVENTION

The polyhistidine-tag (His-tag) is widely used for protein purification, detection and immobilization[1]. Majority of expression vectors use six consecutive histidine residues tag ($His_6$-tag) fused to the protein of interest with or without flexible linkers[2]. In general, fast and selective detection of His-tagged proteins is desired.

As an alternative to traditional immuno-detection with anti-His antibodies, metal ion-chelating nitrilotriacetate (NTA) moiety (monoNTA, monovalent N-nitriloacetic acid) offers easier detection and eliminates the need for costly antibodies[3,4]. Careful chemical and geometrical considerations have led to the assembly of NTA moiety into higher order structures, termed multivalent chelator heads (MCHs). The multivalent metal affinity interactions of $Ni^{2+}$-loaded MCHs (as in the case of cyclic trisNTA) increase the affinity towards $His_6$-tag by a 1000-fold relative to $Ni^{2+}$-monoNTA[5-9]. The use of fluorescently labeled MCHs have been applied in protein detection in polyacrylamide gel electrophoresis (PAGE). However, there is still a need for improved methods of protein detection by employing MCHs and PAGE that allow for expanded use of MCHs in PAGE or improved detection limits.

It is an object of the present invention to provide methods for detecting proteins using fluorescently labeled NTA probes and PAGE or blot membranes.

It is also an object of the present invention to provide methods for detecting proteins following PAGE using a UV light source and naked eye or bench camera visualization.

SUMMARY OF THE INVENTION

Methods for detecting His-tagged proteins using NTA probes and polyacrylamide gel electrophoresis (PAGE), preferably, SDS-PAGE, are disclosed.

In one embodiment, the method includes using a metal ion-loaded NTA probe labeled with a UV-excitable fluorophore with visible emission to detect His-tagged protein in a sample, by exposing the gel following separation of the proteins in the sample using PAGE, to a UV-light source. In this embodiment, the protein sample can be contacted with a metal ion-loaded NTA probe labeled with a UV-excitable fluorophore with visible emission before or after being subjected to PAGE. Preferred metal ions in the metal ion-loaded NTA probes include $Ni^{2+}$, $Zn^{2+}$, $Cu^{2+}$, $Cd^{2+}$, $Hg^{2+}$, $Co^{2+}$ and $Fe^{2+}$ among others. In a preferred embodiment, the method incudes contacting the gel following electrophoresis with compositions containing a metal ion-loaded NTA-based probe labeled with a UV-excitable fluorophore with visible emission, to allow binding of the probe to the His-tagged proteins, and detecting the presence of the probe (and therefore of the His-tagged proteins) by exposing the gel to a UV-light source, followed by naked eye or bench camera visualization. In this embodiment, the method can include additional steps of transferring the separated His-tagged proteins onto a western blot membrane, for example, a Polyvinylidene difluoride (PVDF) membrane, blocking the membrane with BSA (bovine serum albumin), and then detecting the presence of the His-tagged proteins on the membrane by exposure to a UV-source, followed by naked eye or bench camera visualization. A particularly preferred UV-excitable probe with visible emission is $Ni^{2+}$-loaded trisNTA$^{Alexa405}$ ($Ni^{2+}$-trisNTA$^{Alexa405}$). The disclosed methods allow protein detection using a UV transilluminator as excitation source and the naked human eye or bench camera as detector, and the methods detect protein concentrations as low as 5 pmol for SDS-PAGE or 2.5 pmol if the protein samples are transferred from the gel onto a western blot membrane.

In another embodiment, the probe is a metal ion-loaded NTA-based probe coupled to a fluorophore with the majority of excitation and emission in the visible region of the electromagnetic spectrum. In this embodiment, the method includes separating proteins in a sample using PAGE, contacting the gel following electrophoresis with a composition containing a fluorescently labeled metal ion-loaded NTA probe to allow binding of the metal ion-loaded NTA probe to the His-tagged proteins, and detecting the presence of the fluorescently labeled and metal ion-loaded NTA probe (and therefore of the His-tagged proteins). In one preferred method, the His-tagged proteins are not contacted with the fluorescently labeled and metal ion-loaded NTA probe prior to subjecting the samples to PAGE i.e., the NTA probe is not subjected to PAGE. Suitable fluorescently labeled metal ion-loaded NTA probes include an NTA moiety (monoNTA or multivalent NTA), conjugated to a fluorophore with the majority of excitation and emission in the visible region of the electromagnetic spectrum. Preferred metal ions in the metal ion-loaded NTA probes include $Ni^{2+}$, $Zn^{2+}$, $Cu^{2+}$, $Cd^{2+}$, $Hg^{2+}$, $Co^{2+}$ and $Fe^{2+}$ among others. Exemplary multivalent NTA moieties include trisNTA and hexaNTA. Exemplary fluorescently labeled and metal ion-loaded NTA probes include $Ni^{2+}$-trisNTA$^{Alexa647}$, $Ni^{2+}$-trisNTA$^{Cy3B}$, and $Ni^{2+}$-hexaNTA$^{Alexa647}$. A preferred fluorescently labeled and metal ion-loaded NTA probe is $Ni^{2+}$-trisNTA$^{Alexa647}$, and the methods allow detection of as low as 0.1 pmol of $His_6$-tagged protein.

In one embodiment, the PAGE process does not include a loading dye such as Bromophenol Blue. However, in some embodiments, the PAGE process includes a loading dye.

The methods in some preferred embodiments include one or more washing steps following incubation of His-tagged protein-containing gels with fluorescently labeled metal ion-loaded NTA probes. The washing steps can include washing, preferably in warm water, for at least 10 minutes, preferably 20 minutes and more preferably, at least 30 minutes, to remove unbound fluorophore conjugates.

DETAILED DESCRIPTION OF THE INVENTION

I. Definitions

Figure 1A:
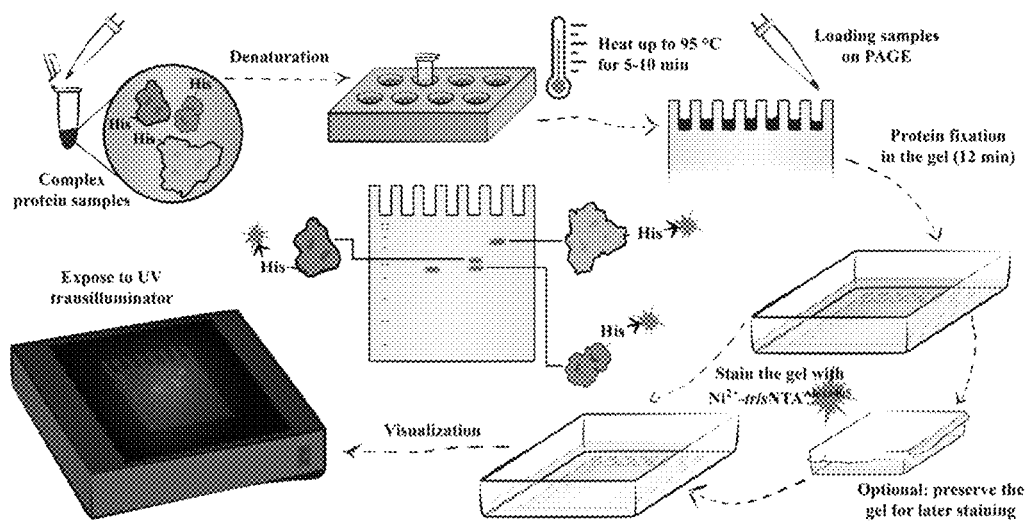
FIG. 1A is a schematic representation of the UVHis-PAGE protocol for UV-based detection of His-tagged proteins in PAGE gels without the requirement of immunoblotting. The driving force of the method is represented by the metal affinity interaction of the metal ion-loaded and fluorescently labeled MCH and the His-tag of the protein of interest. The conjugated fluorophore is UV-excitable with visible emission for visualization by the naked human eye upon exposure to a UV transilluminator.

"Conjugate", and its related terms, refers to the covalent or non-covalent linkage of a molecule to another molecule, or one part of a molecule to a different part of the same molecule. Similarly, the term "linkage chemistry" can refer to the type of linkage between, for example, a fusion protein such as sliding clamp protein/polypeptide and a carrier or surface. The linkage chemistry can involve covalent or non-covalent linkage. Covalent linkages can be direct or indirect (i.e., mediated via a linker). Non-covalent linkage includes electrostatic interactions, hydrogen bonding interactions, affinity interactions, metal coordination, physical adsorption, host-guest interactions, hydrophobic interactions, π-stacking interactions, van der Waals interactions, magnetic interactions, and dipole-dipole interactions.

"Covalent linkage", refers to a bond or organic moiety that covalently links molecules (e.g. fusion proteins) to a non-cellular surface.

The terms "running buffer" refers to the solution used to provide contact between the electrodes and the gel when processing a sample through the gel by electrophoresis.

"Metal ion-loaded NTA probe" as used herein refers to a metal ion-chelating nitrilotriacetate (NTA) loaded with the respective metal ion, labelled with a fluorophore, for example, covalent linkage of the fluorophore with the metal ion-chelating nitrilotriacetate.

II. Compositions

The disclosed methods use metal ion-chelating nitrilotriacetate (NTA) moieties to detect His-tagged proteins. Examples include moieties with one NTA (monoNTA, monovalent N-nitriloacetic acid) or multivalent chelator heads (MCHs), which include >1 NTA. A preferred MCH is trisNTA (trivalent N-nitriloacetic acid), although other MCHs, such as, bisNTA, tetrakisNTA and hexaNTA (hexavalent N-nitriloacetic acid) can be used. hexaNTA is derived from two trisNTA heads that have been coupled via an optimized linker.

In some embodiments, the NTA moiety-based chelator head, for example, MCH, is conjugated to fluorophores (fluorescent tag) such as fluorophores with the majority of excitation and emission in the visible region of the electromagnetic spectrum, either directly, or indirectly, with a spacer, to form a fluorescently labeled NTA-probe. A fluorescently labeled NTA probe that include an MCH is referred to herein as multivalent chelator probe (MCP). The fluorescent tag may be any molecule that emits fluorescent light either naturally or when exposed to radiation such as visible or ultra-violet light.

Any dye that has the majority of its emission and excitation in the visible region of the electromagnetic spectrum (for example, more than 50%, 60% or 70%, etc) can be used in the disclosed NTA probes, so long as the dye is available for coupling chemistry. For example, if an amine-ester coupling is used, the fluorophore should be available as NHS ester. On the other hand, for hexaNTA, the maleimide form is needed for coupling. In effect, any dye that can be chemically coupled to the MCH works. If the dye retains at least 50% of its emission and excitation in the visible region of the electromagnetic spectrum we call it visible dye.

Typical examples include: Alexa Fluor dyes, from Alexa Fluor 430 to 700), Cyanine dyes, Rhodamine-based dyes, Fluorescein-based dyes, Atto dyes, from Atto 425 to Atto 740), etc.

Exemplary fluorophores include cyanine dyes such as Cy3, Cy3B, Cy3.5, Cy5, Cy5.5, Cy7, Cy7.5, and derivatives thereof. A preferred fluorophore is Cy3B, the structure of Cy3B NHS, shown below. These dyes are commercially available. NHS ester form of Cy3B (Cy3B dye N-hydroxysuccinimidyl ester) can be purchased from GE Healthcare.

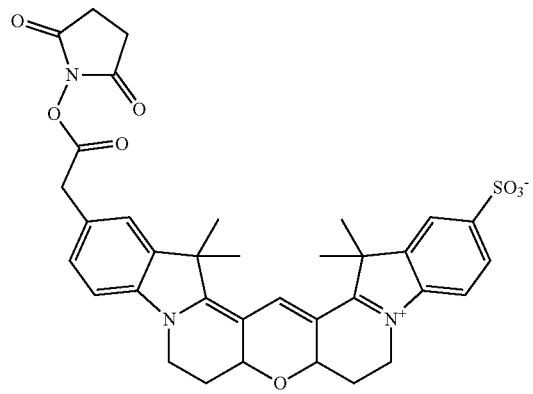

Cy3B NHS

Exemplary fluorophores also include Alexa Fluor dyes and their derivatives. NHS ester forms of Alexa Fluor 647 can be purchased from Thermo Fisher Scientific. The Alexa Fluor family of fluorescent dyes is a series of dyes manufactured by Molecular Probes, now a part of Thermo Fisher Scientific. Exemplary visible Alexa Fluor fluorophores include Alexa Fluor 488, Alexa Fluor 514, Alexa Fluor 594; Alexa Fluor 610; Alexa Fluor 633; Alexa Fluor 635.

Other types of fluorophores useful in the disclosed methods, but not limited to Oregon Green 488, Cy5-analogue FEW S0387.

In one preferred embodiment, the multivalent chelator probe (MCP) is trisNTA (preferably cyclic trisNTA) or hexaNTA, conjugated to Alexa647.

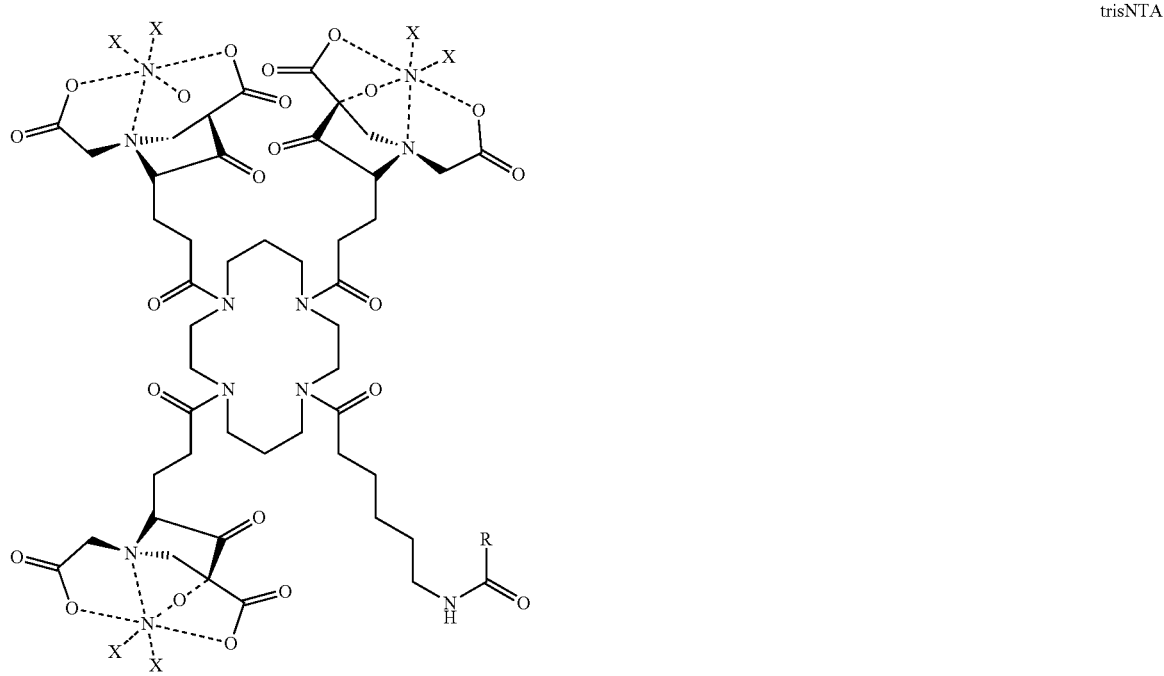

trisNTA

R = Alexa647

7
-continued
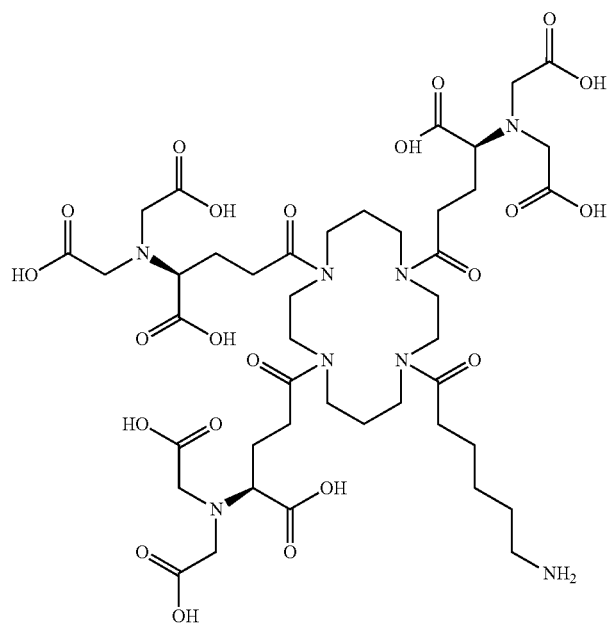
8
trisNTA Amine
hexaNTA
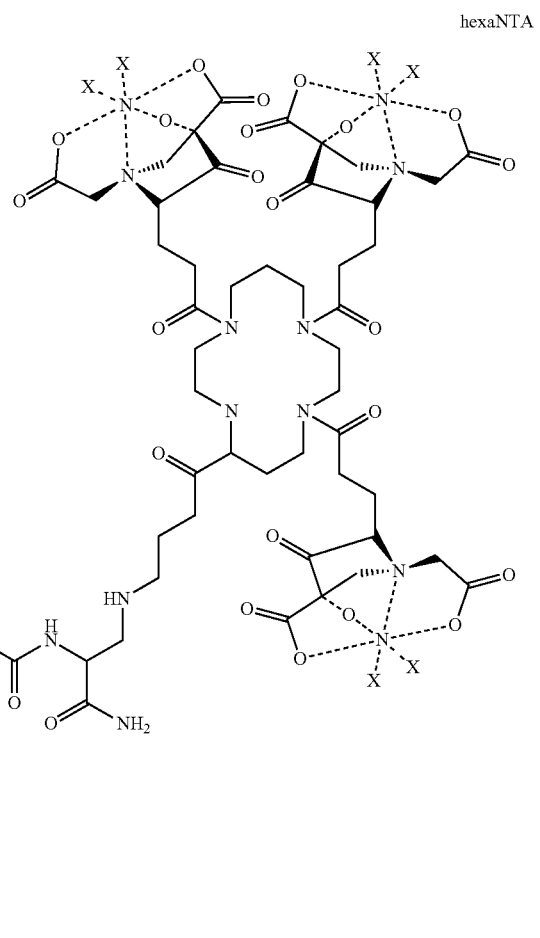

In other embodiments, the MCH is conjugated to a UV-excitable dye that emits in the visible spectrum. A preferred dye is Alexa Fluor 405. These dyes are commercially available. NHS ester forms of Alexa Fluor 405 can be purchased from Thermo Fisher Scientific.

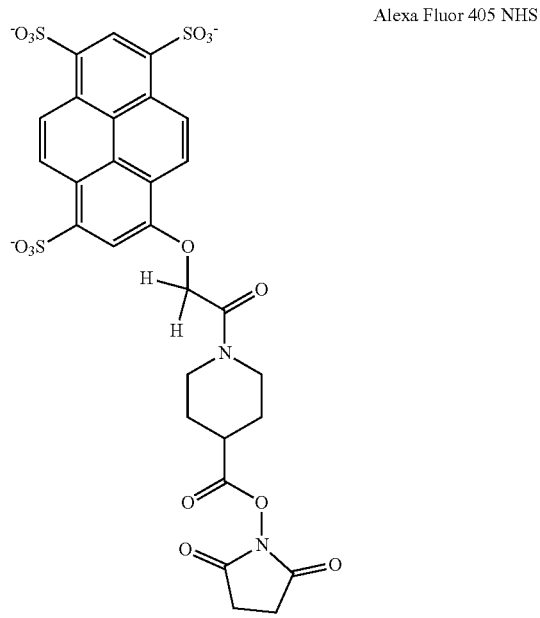

Alexa Fluor 405 NHS

Any dye that has the majority of its emission in the visible region of the electromagnetic spectrum (for example, more than 50%, 60% or 70%, etc) and the majority of its excitation in the UV region of the electromagnetic spectrum (let's say more than 50%, 60% or 70%, etc), can be used in this aspect of the disclosed methods.

Typical examples include: Alexa Fluor 350, Alexa Fluor 405, Atto 390, CF350, CF405M, CF405S, DyLight 350, DyLight 405, HiLyte Fluor 405, HiLyte™ Fluor 405, iFluor 350, iFluor 405, Coumarin-based dyes, Pacific blue and its derivatives, Cascade blue dyes and its derivatives, Pyrene-based dyes.

In all embodiments, the MCP is preferably loaded with metal ions that include $Ni^{2+}$, $Zn^{2+}$, $Cu^{2+}$, $Cd^{2+}$, $Hg^{2+}$, $Co^{2+}$ and $Fe^{2+}$ among others.

III. Method of Making and Using

The disclosed methods are used to detect histidine-labelled proteins, for example, $His_6$-tag, $His_{10}$-tag, or $His_{12}$-tag. The methods preferably use fluorescently labeled and metal ion-loaded NTA probes. The disclosed methods improve the protein detection limit when using MCPs to detect proteins in a sample. The disclosed method improves protein detection by electrophoresis, preferably, polyacrylamide gel electrophoresis, and more preferably, sodium dodecyl sulfate-polyacrylamide gel electrophoresis (SDS-PAGE). The disclosed methods can also be used to detect His-tagged proteins following polyacylamide electgrophoresis procedures using cationic surfactants (CTAB (N-cetyl-N,N,N-trimethylammoniumbromide)-PAGE or benzyldimethyl-n-hexadecylammonium chloride (16-BAC PAGE), or combinations thereof (Nothwang et al., *Two-dimensional separation of membrane proteins by 16-BAC-SDS-PAGE*, in *Methods in Molecular Biology* 528:269-77 (2009).

The disclosed methods include applying a sample containing one or more compounds to be separated to a gel of an electrophoresis apparatus for example, a separating polyacrylamide gel, providing a running buffer; and subjecting the gel to an electric field for sufficient time such that at least one compound in the sample is caused to move into the gel, contacting the gel with separated proteins with a composition containing a fluorescently labeled and metal ion-loaded NTA probe, and detecting the presence of His-tagged proteins in the sample based on the fluorophore of the metal ion-loaded MCP.

SDS-PAGE is an electrophoresis method that allows protein separation by mass. The medium/is a polyacrylamide-based discontinuous gel. About 1.4 grams of SDS bind to a gram of protein, corresponding to one SDS molecule per two amino acids. SDS acts as a surfactant, covering the proteins' intrinsic charge and conferring them very similar charge-to-mass ratios. The intrinsic charges of the proteins are negligible in comparison to the SDS loading, and the positive charges are also greatly reduced in the basic pH range of a separating gel. Upon application of a constant electric field, the protein migrate towards the anode, each with a different speed, depending on its mass. This simple procedure allows precise protein separation by mass. SDS-PAGE systems are known in the art and are routinely used in protein separation. They are also described in U.S. Pat. No. 4,481,094. Some improvements to gels have been made to improve loading. For example, U.S. Pat. No. 5,656,145 issued to Nguyen uses a loading guide so one can direct the samples into the wells without seeing them. Alternate structures, such as plastic ribs or walls have been used to divide sample-loading wells, making them easier to see. Examples of these can be found in U.S. Pat. No. 6,878,257 to Manusu and U.S. patent application Ser. No. 20030141190 by Alpenfels. U.S. Publication No. 20070187252 disclosesinsoluble pigmented materials added to the gel in the loading area to visually differentiate the loading area and sample wells. The Examples in the present application, incorporated here by reference, make and load protein samples for SDS-PAGE.

A. Methods of Making Multivalent Chelator Probes (MCP)

Methods of conjugating MCHs to fluorophores and to load the complexes with metal ions to form metal ion-loaded and fluorescently labeled multivalent chelator probes (MCPs) are known in the art. Piehler et al. synthesized supramolecular entities containing 1-4 NTA moieties and a fluorescein (monoNTA-Fluo, bisNTA-Fluo, trisNTA-Fluo, and tetrakisNTA-Fluo) and characterized their interaction with His-tag ($His_6$ and $His_{10}$-sequences) *J. Am. Chem. Soc.* 2005; 127:10205-10215. Methods of synthesizing MCPs are exemplified in the examples of this application. Fluorophores are commercially available in NHS (N-hydroxysuccinimidyl) ester forms. The amine-NHS coupling reactions can be performed according to the well-established protocol described in, generally following the protocol described in Batoschik, et al., Scientific Reports, |(2018) 8:4977|DOI: 10.1038/s41598-018-23154-3, for example[8,9].

The conjugates are purified over a reversed-phase C18 (Sigma-Aldrich) column by using an HPLC system, verified by MALDI-TOF-MS and loaded with Ni (II), identically to the steps described in[8,9]. After incubation with Ni (II), the conjugates can be purified over a 1 ml HiTrap Q HP (GE Healthcare) column and eluted with a 0-2.5 M NaCl gradient using an FPLC system. It is worth noting that $Ni^{2+}$-trisNTA conjugates with Cy3B and Alexa Fluor 647 can be eluted at less than 1 M NaCl concentration, while the $Ni^{2+}$-trisNTA conjugate with Alexa Fluor 405 can require up to ~1.6 M NaCl for complete elution.

B. Methods of Detecting His-Tagged Proteins

An oligohistidine sequence ((His) n, n≥6, in general) called His-tag is known to interact robustly with transition-metal ions complexes, including nitrilotriacetic acid (NTA) complex of $Ni^{2+}$, thereby the sequence is widely used for purification of expressed proteins by affinity chromatography. The selective interaction between His-tag and the metal complexes is also applicable for site-specific fluorescent labeling of proteins. This strategy has important and unique advantages, including the compatibility to the large library of existing His-tagged proteins.

i. Post-Run Staining Method of Detecting His-Tagged Proteins by Metal Ion-Loaded MCPs with Visible Excitation and Emission.

The post-run staining method disclosed herein separates the proteins in a sample using electrophoresis, and the sample loaded onto the gel does not include the MCP.

A sample containing His-tagged protein is separated by PAGE as follows. First, the protein sample is mixed with PAGE sample buffer, for example, SDS-PAGE electrophoresis sample buffer, heated at 95° C. and run on 10% SDS-PAGE. An exemplary electrophoresis sample buffer is 10% SDS, 500 mM DTT, 50% Glycerol, 250 mM Tris-HCl, pH 6.8); "Tris" is tris(hydroxymethyl)aminomethane. SDS contained in the sample buffer denatures proteins and make them negatively charged. In this manner, each protein will migrate in the electrophoretic field in a measure proportional to its length. SDS binds strongly to proteins at an approximate ratio of 1 dodecyl sulfate molecule per 2 amino acid residues. Therefore, the negative charge/unit mass ratio when SDS is bound to the polypeptide chain is similar for all proteins. Glycerol increases the density of the sample relative to the surrounding running buffer making it easier to load in the well. The sample is preferably mixed with 5× electrophoresis sample buffer. The sample is then loaded onto a gel. Precast and packaged gels in a wide variety of gel formulations, acrylamide percentages, thicknesses, well formats, and buffer systems are commercially available from several manufacturers. The disclosed methods are exemplified using 10% SDS-PAGE gels (Invitrogen NuPAGE 10% Bis-Tris gels, 10 wells and 1.0 mm thickness). However, it is within the abilities of one of ordinary skill in the art to select a gel type based on the characteristics of the protein to be detected.

The gels are run in an SDS running buffer, for example, 1×MOPS SDS running buffer (Invitrogen Novex 20× NuPAGE MOPS SDS Running Buffer). In a preferred embodiment, the electrophoresis sample buffer did not contain any loading dye such as Bromophenol Blue. In a particularly preferred embodiment, the sample loaded onto the gel does not include the MCP i.e., the MCP is not subjected to the SDS-PAGE.

After the running step, the gels are fixed with 1× fixation solution, for example (40% methanol, 20% glacial acetic acid and 40% water) while heating in the microwave for 2 min and cleaned with water while heating for 10 min in the microwave.

After the fixation and washing of the gels, the gels can then be contacted with the $Ni^{2+}$-MCP i.e., the staining step. The protocol can proceed directly to the staining step or the gel can be kept in water for future staining with minimal diffusion of the bands (FIG. 1A). Gel staining can be performed as exemplified herein using $Ni^{2+}$-monoNTA$^{Atto647N}$, $Ni^{2+}$-trisNTA$^{Alexa647}$, $Ni^{2+}$-monoNTA$^{Atto550}$, and $Ni^{2+}$-trisNTA$^{Cy3B}$. Briefly, the gels can be submerged in 1×PBS (Phosphate buffered saline) containing 150 nM $Ni^{2+}$-monoNTA$^{Atto647N}$ or $Ni^{2+}$-trisNTA$^{Alexa647}$, or 300 nM $Ni^{2+}$-monoNTA$^{Atto550}$ or $Ni^{2+}$-trisNTA$^{Cy3B}$ for an amount of time that allows staining to proceed. As exemplified herein, the gels were submerged in these solutions and staining was allowed to proceed for 1 hr at room temperature, with gentle shaking in the dark.

After the completion of the staining step, the gels are preferably rinsed with water to remove the excess staining solution. In order to remove unbound fluorophore conjugates and reduce the background, the gels are preferably submerged in warm water and gently shaken in the dark for 30, 60 or 90 min; warm water is intended to facilitate the diffusion out of the gels of the unbound fluorophore conjugates. After the washing cycle, the gels are imaged using a suitable imaging system with appropriate excitation source and emission filters, exemplified herein using an Amersham Typhoon biomolecular laser scanner (GE Healthcare).

ii. Methods for Detecting His-Tagged Proteins in Samples Following SDS-PAGE Using UV-Excitation and Naked Eye or Bench Camera Visualization.

A method of detecting His-tagged proteins in a sample using UV-excitation and naked eye or bench camera visualization and SDS-PAGE is disclosed. In a preferred embodiment, the protein is His-tagged, and is detected using a metal ion-loaded MCH conjugated to a UV-excitable dye with visible emission (UVHis-PAGE). The His-tagged protein is detected using a UV-light source. A preferred conjugated dye is Alexa Fluor 405. The method includes contacting the protein sample with the UV-excitable metal ion-loaded MCP before or after subjecting the sample to PAGE. In a preferred embodiment, the method includes contacting the gel following electrophoresis with a composition comprising an effective amount of a UV-excitable metal ion-loaded MCP for an effective amount of time and under suitable conditions to allow binding of the UV-excitable metal ion-loaded MCP to His-tagged proteins on the gel, and detecting the presence of the probe by exposing the gel to a UV-light source and visualizing the gel with the human naked eye or a bench camera. An effective amount of a UV-excitable metal ion-loaded MCP, an effective amount of time and suitable conditions to allow binding of the UV-excitable metal ion-loaded MCP is exemplified herein by submerging the gels in an UV-excitable metal ion-loaded MCP-containing solution (containing 2 uM $Ni^{2+}$-trisNTA$^{Alexa405}$) and incubating for 1 hr in the dark with gentle shaking. It should be noted that the concentration of the MCP, staining time, shaking (or lack thereof) and the presence of light (or lack thereof) can be varied and the ability to do so is within ordinary skill in the art.

A particularly preferred UV-excitable metal ion-loaded MCP is $Ni^{2+}$-trisNTA$^{Alexa405}$.

However, Any combination of an NTA-based chelator head (such as mono, bis, tris, tetrakis, hexa, etc.) and a UV-excitable dye as defined above (such as Alexa Fluor 350, Alexa Fluor 405, Atto 390, CF350, CF405M, CF405S, DyLight 350, DyLight 405, HiLyte Fluor 405, HiLyte™ Fluor 405, iFluor 350, iFluor 405, Coumarin-based dyes, Pacific blue and its derivatives, Cascade blue dyes and its derivatives, Pyrene-based dyes.). Additionally, any probe preferably includes a loaded metal ion. In all embodiments, the MCP is preferably loaded with metal ions that include $Ni^{2+}$, $Zn^{2+}$, $Cu^{2+}$, $Cd^{2+}$, $Hg^{2+}$, $Co^{2+}$ and $Fe^{2+}$ among others.

The methods using UV-excitable metal ion-loaded MCP in some embodiments include the additional steps of transferring the proteins separated by PAGE onto a western blot membrane, blocking the membrane using a suitable protein such as BSA (bovine serum albumin), and then exposing the membrane to the UV source, followed by detection using the naked human eye or bench camera. Methods of transferring proteins following separation by PAGE are known in the art, and are exemplified herein with the following steps.

Following SDS-PAGE, the proteins are transferred to a suitable western blot membrane such as a PVDF membrane (Merck) by using the sandwich method. There are two common membrane types used for western blot analysis: PVDF and nitrocellulose. PVDF is generally better for low molecular weight proteins. This membrane can be purchased in different pore sizes. For proteins less than 30 kD, the pore size of 0.2 μM PVDF is recommended over the 0.45 μM pore size.

The transfer is performed under a constant electric current of 0.39 A for 90 min. The transfer buffer can include 25 mM Tris-base, 192 mM glycine, both dissolved in ddH2O and 20% (v/v) methanol. After the transfer, the membrane is washed once with 1× Tris Buffered Saline containing Tween 20 (TBST). Afterwards, the membranes were blocked for 1 hour shaking at room temperature using 5% (w/v) Bovine Serum Albumin (BSA) dissolved in 1× TBST. Following that, the membranes were washed once with 1×TBST.

For the staining step (i.e., contacting the protein sample with the UV-excitable metal ion-loaded MCP), both the gel and the membrane are in the same way, described above, i.e., like the gels, the membrane us submerged in a solution containing the UV-excitable metal ion-loaded MCP comprising an effective amount of a UV-excitable metal ion-loaded MCP for an effective amount of time and under suitable conditions to allow binding of the UV-excitable metal ion-loaded MCP to His-tagged proteins on the membrane.

The membrane is rinsed for example, with 1×TBST and exposed to UV transilluminator equipped with a protective screen.

In the case of the blot membrane, washing in the gel in the presence of at least 50 mM EDTA allows to get rid of the bound UV-excitable metal ion-loaded MCP, for example, $Ni^{2+}$-trisNTA$^{Alexa405}$ and reuse the membrane for future experiments.

EXAMPLES

Methods
Protein Expression and Purification

To purify $His_6$-SUMO, the empty expression plasmid pE-SUMO (LifeSensors) was transformed into BL21 (DE3) E. coli expression strain (Novagen). 2 l of 2×YT (Teknova) media supplemented with 50 mg/l Kanamycin was inoculated from an overnight pre-culture and grown at 37° C. When the cell growth reached an $OD_{600}$ of 0.8, expression was induced by the addition of 0.1 mM Isopropyl β-D-1-thiogalactopyranoside (IPTG) and incubation continued for additional 4 hr at 37° C. The soluble fraction of the cell lysate was applied onto a 5 ml HisTrap HP (GE Healthcare) affinity column and the protein was eluted with 350 mM Imidazole. The eluted protein was concentrated and further purified over a 120 ml Superdex 75 pg size-exclusion column (GE Healthcare). All these steps were performed using an FPLC system.

Synthesis of Fluorescent Multivalent Chelator Probes $Ni^{2+}$-monoNTA conjugates of Atto550 and Atto647N were purchased from Sigma-Aldrich.

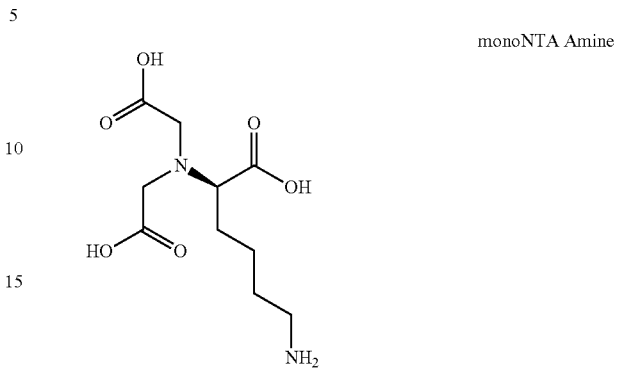

monoNTA Amine trisNTA amine was purchased from Toronto Research Chemicals. NHS ester forms of Alexa Fluor 405 and Alexa Fluor 647 (shown below) were purchased from Thermo Fisher Scientific. NHS ester form of Cy3B was purchased from GE Healthcare.

Alexa Fluor 647 NHS

Figure 1B:
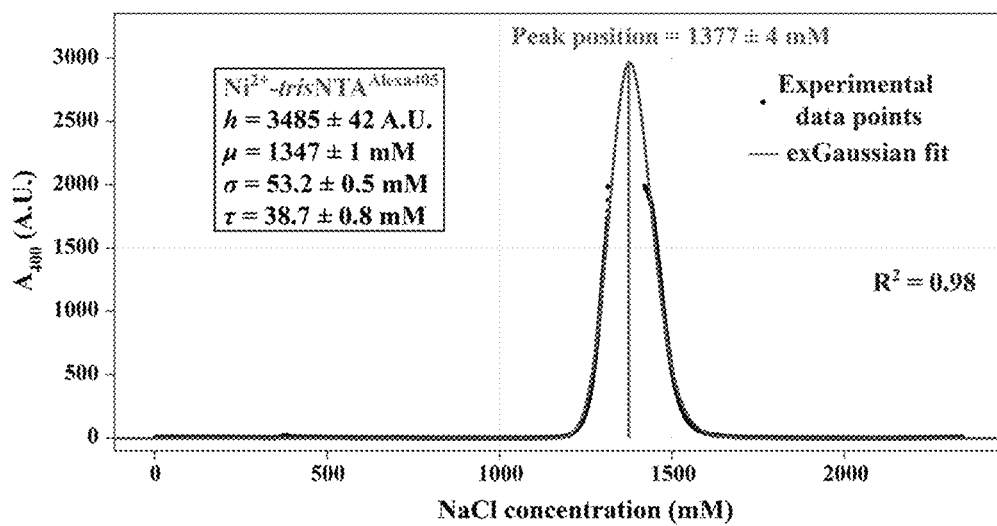
FIG. 1B shows fitting of the elution peak of $Ni^{2+}$-trisNTA$^{Alexa405}$ from the HiTrap Q 1 ml column by the EMG model. The values of the EMG parameters are shown in the inset table with their 95% confidence interval. The vertical red line represents the position of the maximum of the elution peak as calculated from the fitting parameters as described in the Methods section of the Examples. This value together with its 95% confidence interval is also reported above the peak. Datapoints above 2000 A.U. were removed, due to the spectrophotometer detector saturation.

The amine-NHS coupling reactions were performed according to the well-established protocol described in[8,9]. The conjugates were purified over a reversed-phase C18 (Sigma-Aldrich) column by using an HPLC system, verified by MALDI-TOF-MS and loaded with Ni (II), identically to the steps described in[8,9]. After incubation with Ni (II), the $Ni^{2+}$-loaded conjugates were purified over a 1 ml HiTrap Q HP (GE Healthcare) column and eluted with a 0-2.5 M NaCl gradient using an FPLC system. It is worth noting that $Ni^{2+}$-trisNTA conjugates of Cy3B and Alexa Fluor 647 were eluted at less than 1 M NaCl concentration, while the $Ni^{2+}$-trisNTA conjugate of Alexa Fluor 405 required up to ~1.6 M NaCl for complete elution (FIG. 1B).

SDS-PAGE Running and Staining

Samples of interest were mixed with 5× electrophoresis sample buffer (10% SDS, 500 mM DTT, 50% Glycerol, 250 mM Tris-HCl, pH 6.8), heated up for 10 min at 95° C., and then loaded onto 10% SDS-PAGE gels (Invitrogen NuPAGE 10% Bis-Tris gels, 10 wells and 1.0 mm thickness). The gels were run in 1×MOPS SDS running buffer (Invitrogen Novex 20× NuPAGE MOPS SDS Running Buffer). Intentionally, the electrophoresis sample buffer did not contain any loading dye that could interfere with the image acquisition.

For CBB staining, the gels were stained with 1× staining solution (40% methanol, 20% glacial acetic acid, 40% water and 0.3% (w/v) Coomassie Brilliant Blue G-250) while heating in the microwave for 1 min and destained with water while heating for 10 min in the microwave.

For NTA-based detection, the gels were fixed with 1× fixation solution (40% methanol, 20% glacial acetic acid and 40% water) while heating in the microwave for 2 min and cleaned with water while heating for 10 min in the microwave. The gels were then submerged in 1×PBS containing 150 nM $Ni^{2+}$-monoNTA$^{Atto647N}$ or $Ni^{2+}$-trisNTA$^{Alexa647}$, 300 nM $Ni^{2+}$-monoNTA$^{Atto550}$ or $Ni^{2+}$-trisNTA$^{Cy3B}$ or 2 μM $Ni^{2+}$-trisNTA$^{Alexa405}$. The gels were incubated in these solutions for 1 hr with gentle shaking in the dark, rinsed with water and destained in warm water for different amount of time as indicated in each case.

Immunoblotting

Following SDS-PAGE, the proteins were transferred to PVDF membrane (Merck) by using the sandwich method. The transfer was performed under a constant electric current of 0.39 A for 90 min. The transfer buffer contained 25 mM Tris-base, 192 mM glycine, both dissolved in ddH2O and 20% (v/v) methanol. After the transfer, the membranes were washed once with 1× Tris Buffered Saline containing Tween 20 (TBST). Afterwards, the membranes were blocked for 1 hour shaking at room temperature using 5% (w/v) Bovine Serum Albumin (BSA) dissolved in 1×TBST. Following that, the membranes were washed once with 1×TBST and then were incubated with the anti-Histidine Tag antibody (Bio-Rad, MCA1396) at a concentration of 1 μg/mL for the indicated amount of time, depending on the experiment. Then, three washes of 5 min each took place, using 1×TBST. Next, the membranes were incubated for 30 min at room temperature shaking with the anti-mouse IgG, HRP-conjugated antibody (Cell Signaling, 7076) at a concentration of 0.1 μg/mL. Afterwards, three washes of 5 min each were performed and then the membranes were incubated for 2 min with the chemiluminescent substrate (SuperSignal West Pico, Thermo Fisher, 34080) before imaging.

Gel and Membrane Imaging

CBB-stained gels were imaged under white light by using an iBright CL1000 system (Thermo Fisher Scientific) or by a regular phone photo camera. The antibody-based immunoblotting membranes were imaged with the iBright CL1000 system under chemiluminescence mode. $Ni^{2+}$-trisNTA$^{Alexa405}$ stained gels and membranes were exposed to the UV light generated by UV transilluminator of the FluorChem Q Image analysis system (Alpha Innotech) and imaged with the camera of the same system or by a regular phone photo camera. The Atto550, Cy3B, Atto647N and Alexa Fluor 647 conjugate-stained gels were imaged with an Amersham Typhoon biomolecular laser scanner (GE Healthcare).

Brightness Determination for the Fluorophore Conjugates

For the fluorophores in their free NHS ester form, molecular fluorescence brightness ($B^{Free}$) was calculated, using reference values for the molar extinction coefficient (ε) at the maximum of absorption (Amax) and for the fluorescence quantum yield ($\phi^{Free}$), as previously described in[23]:

$$B_{\lambda_{max}}^{Free} = \varepsilon_{\lambda_{max}} \times \phi^{Free} \quad (1)$$

For the $Ni^{2+}$-trisNTA-fluorophore conjugates we opted to determine the fluorescence brightness ($B^{Coupled}$), via the measured fluorescence lifetime (τ), rather than directly through the fluorescence quantum yield which is more error-prone in measurements.

Assuming an energy or electron transfer mechanism in the excited state between the fluorophore and the $Ni^{2+}$ ions loaded on the conjugate[24], implies that the radiative rate of the fluorescence decay ($k_r$) remains largely unchanged between the free and coupled forms. Only the non-radiative component increases in magnitude to accommodate also the rate of the energy transfer. Under this condition, in both the free and coupled forms the relationships between the fluorescence quantum yields ($\phi^{Free}$ and $\phi^{Coupled}$) and measured fluorescence lifetimes ($\tau^{Free}$ and $\tau^{Coupled}$) can be written as:

$$\begin{cases} \phi^{Free} = k_r \times \tau^{Free} \\ \phi^{Coupled} = k_r \times \tau^{Coupled} \end{cases} \quad (2)$$

Under the above-mentioned assumption of unchanged radiative rate of the fluorescence decay ($k_r$), the system of two equalities is algebraically reduced to:

$$\frac{\phi^{Free}}{\phi^{Coupled}} = \frac{\tau^{Free}}{\tau^{Coupled}} \Rightarrow \phi^{Coupled} = \phi^{Free} \times \frac{\tau^{Coupled}}{\tau^{Free}}. \quad (3)$$

Adapting the indices in Eq. (1) to the case of the coupled fluorophore and by using Eq. (3), the brightness of $Ni^{2+}$-trisNTA-fluorophore conjugates is immediately given as:

$$B_{\lambda_{max}}^{Coupled} = \varepsilon_{\lambda_{max}} \times \phi^{Coupled} = \varepsilon_{\lambda_{max}} \times \phi^{Free} \times \frac{\tau^{Coupled}}{\tau^{Free}} = B_{\lambda_{max}}^{Free} \times \frac{\tau^{Coupled}}{\tau^{Free}}. \quad (4)$$

Here we also assumed that static quenching mechanisms are absent, such that nonfluorescent complexes are not formed and the molar extinction coefficient (ε) remains largely unchanged. Moreover, we assumed the lack of bathochromic and hypsochromic shifts in the absorption spectra, such that $\lambda_{max}$ remains largely unchanged. By using reference values for $B^{Free}_{\lambda_{max}}$ and $\tau^{Free}$ with these considerations, the determination of the brightness of the $Ni^{2+}$-trisNTA-conjugated fluorophore is reduced to the measurement of its fluorescence lifetime. Time-resolved fluorescence lifetime measurements were carried out, as previously described[25,26], using QuantaMaster 800 spectrofluorometer (Photon Technology International Inc.) equipped with a Fianium supercontinuum fiber laser source (Fianium, Southampton, U.K.) operating at 20 MHz repetition rate. Arrival time of each photon was measured with a Becker-Hickl SPC-130 time-correlated single photon counting module (Becker-Hickl GmbH, Berlin, Germany). Measurements were collected under magic angle (54.7°) conditions and photons were counted using time to amplitude converter (TAC). In all measurements, 10.000 counts were acquired. The instrument response function (IRF) was estimated using a Ludox colloidal silica suspension dissolved in water.

Measurements were recorded at room temperature in PBS. All samples were excited at their wavelength of maximum excitation and emission was collected at their wavelength of maximum emission with 5 nm slit width for both excitation and emission. The fluorophores lifetime decays were then obtained using FluoFit software package (PicoQuant) applying the IRF and fitted to two-exponential decays. The best fit was chosen based on reduced chi-square and randomness of the residuals. The reported lifetimes are the mean of amplitude-averaged lifetimes of three independent replicates.

Analysis of the Elution Profile of $Ni^{2+}$-trisNTA$^{Alexa405}$ from the HiTrap Q Column The measured $A_{400}$ values of the $Ni^{2+}$-trisNTA$^{Alexa405}$ elution profile were monitored continuously by using the integrated spectrophotometer module of an FPLC system. This measured elution profile was fitted to an Exponentially-Modified Gaussian (EMG) profile as previously described in[26-30]. First, baseline subtraction routine was applied using the built-in function of the GE Unicorn software. The elution peak was fitted to an EMG profile described by either one of the below equations:

$$\begin{cases} A_{400}(c; h, \mu, \sigma, \tau) = \frac{h\sigma}{\tau}\sqrt{\frac{\pi}{2}}\exp\left(\frac{1}{2}\left(\frac{\sigma}{\tau}\right)^2 - \frac{c-\mu}{\tau}\right)\text{erfc}*\left(\frac{1}{\sqrt{2}}\left(\frac{\sigma}{\tau}\right) - \frac{c-\mu}{\sigma}\right) \\ A_{400}(c; h, \mu, \sigma, \tau) = h\exp\left(-\frac{1}{2}\left(\frac{c-\mu}{\sigma}\right)^2\right)\frac{\sigma}{\tau}\sqrt{\frac{\pi}{2}}\text{ erfcx}*\left(\frac{1}{\sqrt{2}}\left(\frac{\sigma}{\tau} - \frac{c-\mu}{\sigma}\right)\right) \end{cases},$$

where c represents the current salt (NaCl) concentration, h is the amplitude of the Gaussian which is proportional to the eluted $Ni^{2+}$-trisNTA$^{Alexa405}$ amount and to its molar extinction coefficient, μ and σ are the mean and the standard deviation of the Gaussian part of the model and τ is the relaxation time of the exponential part of the model. Erfc and erfcx are the regular and the scaled complementary error functions. The elution peak was fitted with one of the above-mentioned functions using the cftool of MATLAB software. After obtaining the fitting parameters μ, σ and τ, the main parameter of interest, namely the mode, i.e. the position of the elution peak maximum was determined as:

Results

In order to build the UV-based detection system for $His_6$-tagged proteins in PAGE and blot membrane, two initial choices must be made: a chelator head and an UV-excitable dye with visible emission. However, given the lack of sensitivity of chelator heads to $His_6$-tag[17], optimization of the staining procedure that maximizes their detection limit must be established first.

Choice of Chelator Head and Staining Method for High Sensitivity Fluorescence Detection The hypothesis was that reducing the harsh conditions of SDS-PAGE during the initial incubation and complex migration in the pre-run staining protocol[17], can increase the performance of a given chelator head in detection. Therefore, a post-run staining protocol was implemented (FIG. 1A), which enabled us to directly compare the detection limit of $Ni^{2+}$-monoNTA- and $Ni^{2+}$-trisNTA-coupled fluorophores. To evaluate this hypothesis, a $His_6$-SUMO fusion protein, which bears a single $His_6$-tag at the N-terminus (therefore any amount of protein (described in mol) will correspond to the same amount of $His_6$) was used. This protein fusion was preferred due to its relatively small size, which minimizes the chance of unspecific binding.

Various amounts (0.1-25 μmol) of $His_6$-SUMO were mixed with SDS-PAGE electrophoresis sample buffer, heated at 95° C. and run on 10% SDS-PAGE, as described in the Methods section. Each sample was prepared as double loading volume (30 μl) and then split into two independent gels. This procedure was repeated four times, once for each of the tested fluorophore-chelator heads conjugates: $Ni^{2+}$-monoNTA$^{Atto550}$, $Ni^{2+}$-trisNTA$^{Cy3B}$, $Ni^{2+}$-monoNTA$^{Atto647N}$ and $Ni^{2+}$-trisNTA$^{Alexa647}$. One copy of each gel was transferred to PVDF membrane and immuno-blotted overnight with commercial anti-His antibody and imaged with chemiluminescence (first rows in FIGS. 3A-3D). This immunoblotting step serves as two-fold purpose. First, it ensures that equal amounts of $His_6$-SUMO are loaded on each of the four replicated gels. Second, it illustrates the detection limit of typical anti-His antibody-based immunoblotting as ~0.1 pmol (first rows in FIGS. 3A-D).

The second copy of each of the four gels was fixed using the fast protocol (12 min) described in the Methods section under Examples. After the fixation and washing of the gels, the protocol can proceed directly to the staining step or the gel can be kept in water for future staining with minimal diffusion of the bands (FIG. 1A). For the gel staining step, fresh PBS solutions containing 150 nM $Ni^{2+}$-monoNTA$^{Atto647N}$ or $Ni^{2+}$-trisNTA$^{Alexa647}$ and 300 nM $Ni^{2+}$-monoNTA$^{Atto550}$ or $Ni^{2+}$-trisNTA$^{Cy3B}$ were prepared. The gels were submerged in these solutions and staining was allowed to proceed for 1 hr at room temperature, with gentle shaking in the dark.

After completion of the staining step, the gels were rinsed with water to remove the excess staining solution. In the initial trials, the gels were imaged immediately, nevertheless this resulted in excessive background, especially given the high sensitivity of the laser-based Typhoon scanner (data not shown). In order to remove the unbound fluorophore conjugates and reduce the background, the gels were submerged in warm water and gently shaken in the dark for 30, 60 or 90 min; warm water is intended to facilitate the diffusion out of the gels of the unbound fluorophore conjugates. After each 30 min washing cycle, the gels were imaged using the same Typhoon imaging conditions with appropriate excitation source and emission filters.

Figure 3A:
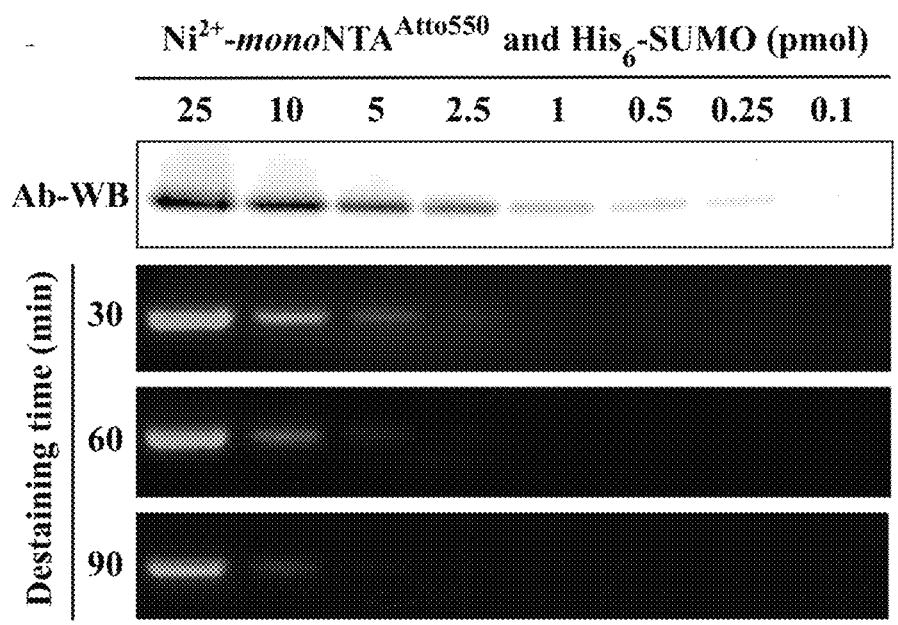
FIGS. 3A-3D show the comparison of the detection performance of $Ni^{2+}$-monoNTA and $Ni^{2+}$-trisNTA fluorescent conjugates in SDS-PAGE. Each gel was run in duplicate and one copy was stained post-run and fixation with (FIG. 3A) $Ni^{2+}$-monoNTA$^{Atto550}$, (FIG. 3B) $Ni^{2+}$-trisNTA$^{Cy3B}$, (FIG. 3C) $Ni^{2+}$-monoNTA$^{Atto647}$ and (FIG. 3D) $Ni^{2+}$-trisNTA$^{Alexa647}$. The gels were destained for the indicated amount of time (30, 60 or 90 min) and imaged using a Typhoon laser-based scanning system (rows 2-4 in each panel). The second copy of each gel was used for immunoblotting using anti-His antibody (Ab-WB, first row in each panel).
Figure 3B:
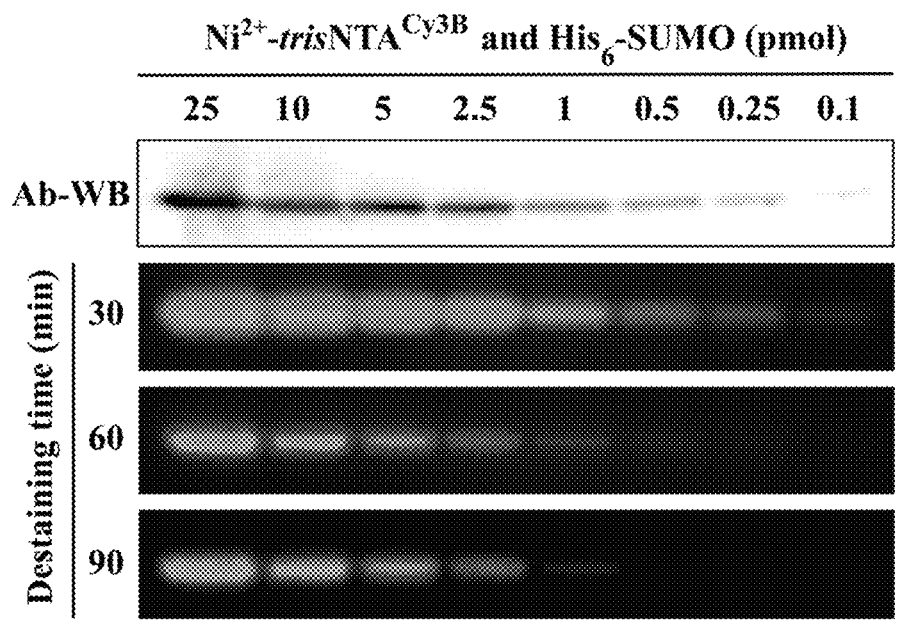
Figure 3C:
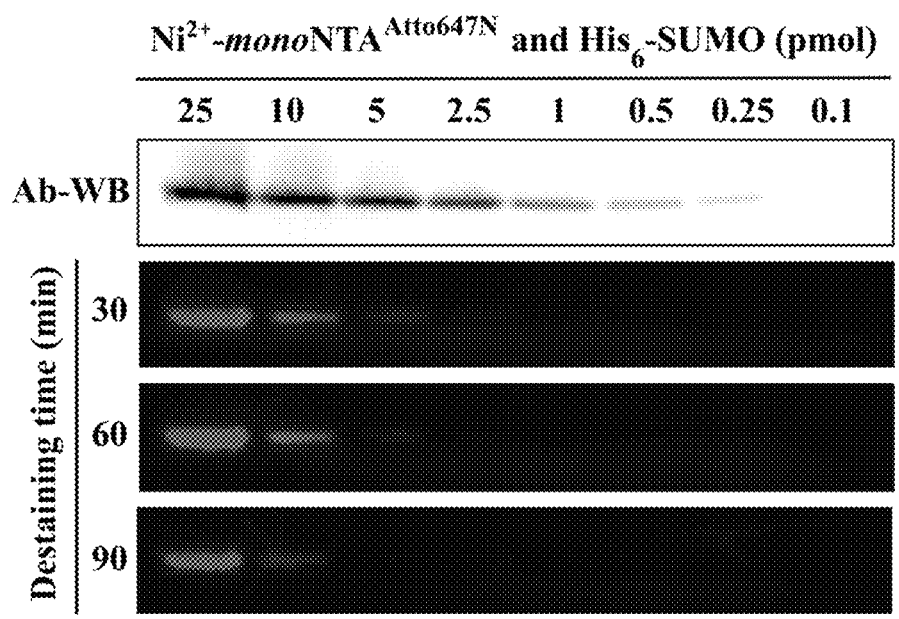
Figure 3D:
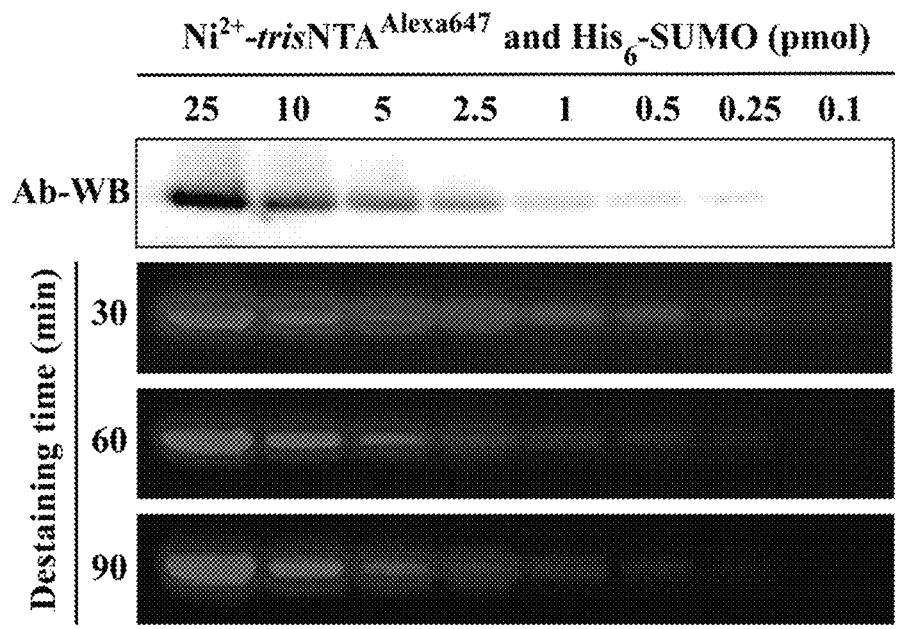

After the first 30 min of destaining and imaging cycle, both $Ni^{2+}$-trisNTA conjugates exhibited a detection limit of ~0.1 pmol of $His_6$-SUMO (FIGS. 3B, 3D), while the $Ni^{2+}$-monoNTA conjugates were considerably less sensitive with a detection limit of only ~2.5 pmol (FIGS. 3A, 3C). This renders the $Ni^{2+}$-trisNTA conjugates to be ~25-fold more sensitive than $Ni^{2+}$-monoNTA. Each additional 30 min destaining step caused the loss of detection of the last previous band for both $Ni^{2+}$-trisNTA and $Ni^{2+}$-monoNTA conjugates. Nevertheless, from a quantitative point of view, this translates into the loss of only ~0.15-0.5 pmol/30 min for $Ni^{2+}$-trisNTA and ~1-5 pmol/30 min for $Ni^{2+}$-monoNTA. Therefore, in addition to the decreased detection limit, $Ni^{2+}$-trisNTA conjugates also exhibit ~10-fold increased stability overtime as compared to $Ni^{2+}$-monoNTA conjugates. Taken together, these results demonstrate that post-run protocol improved the detection by $Ni^{2+}$-trisNTA conjugates to a level that matches the limit of typical anti-His antibody-based immunoblotting.

UV-Excitable Dye: Trading Sensitivity for Simplicity in Detection

Equipped with the established high resolution detection under post-run staining conditions, the next studies evaluated the choice of the fluorophore for building a UV-based detection system for $His_6$-tagged proteins. Typical UV transilluminators offer a very limited number of wavelength choices, such as 302 and 365 nm. With these considerations, by surveying the absorption spectra, molecular extinction coefficients and quantum yields of commercially available UV-excitable fluorophores, Alexa Fluor 405 was selected (shown below). At 365 nm, this fluorophore retains ~68% of its maximum molar extinction coefficient (FIG. 2B). Nevertheless, it exhibits a relatively lower brightness, which is typical for small organic UV fluorophores (FIG. 2C and Table 1).

Moreover, Alexa Fluor 405 is directly available as NHS ester for the convenience of coupling to the amine-containing chelator heads.

Subsequent studies proceeded to determine the detection limit of $His_6$-tagged in SDS-PAGE and blot membrane using $Ni^{2+}$-trisNTA$^{Alexa405}$. The samples were prepared as described in the previous section, but in the concentration range of 1-1000 pmol $His_6$-SUMO. Each sample was prepared as double loading volume (30 μl) and then split into two independent gels. One copy of the gel was transferred to PVDF membrane and blocked with BSA for 1 hr The second copy of the gel was fixed using the fast protocol (12 min). After rinsing, both the gel and the membrane can be stained immediately or kept for future staining.

Figure 4A:
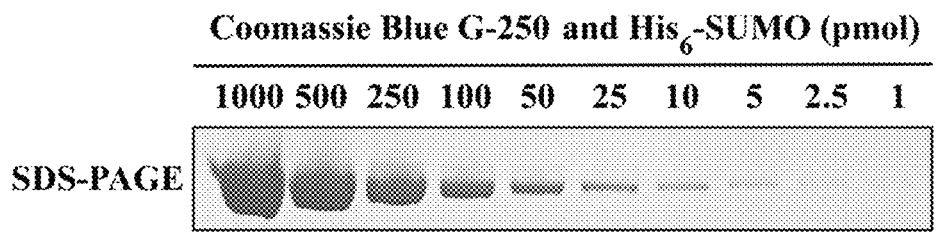
FIGS. 4A-4G show the performance of $Ni^{2+}$-trisNTA$^{Alexa405}$ in the UVHis-PAGE protocol and comparison with Coomassie Brilliant Blue (CBB) staining. CBB-stained SDS-PAGE was imaged with a regular phone photo camera (FIG. 4A) and gel-dock camera (FIG. 4B). $Ni^{2+}$-trisNTA$^{Alexa405}$-stained SDS-PAGE was illuminated by a UV transilluminator and imaged in the dark with a regular phone photo camera (FIG. 4C) and gel-dock camera (FIG. 4D). An additional copy of these gels was transferred to a blot membrane, blocked with BSA, stained with $Ni^{2+}$-trisNTA$^{Alexa405}$, illuminated by a UV transilluminator and imaged in the dark with a regular phone photo camera (FIG. 4E) and gel-dock camera (FIG. 4F). $Ni^{2+}$-trisNTA$^{Alexa405}$-stained blot membrane can also be clearly visualized even under ambient light conditions (FIG. 4G).
Figure 4B:
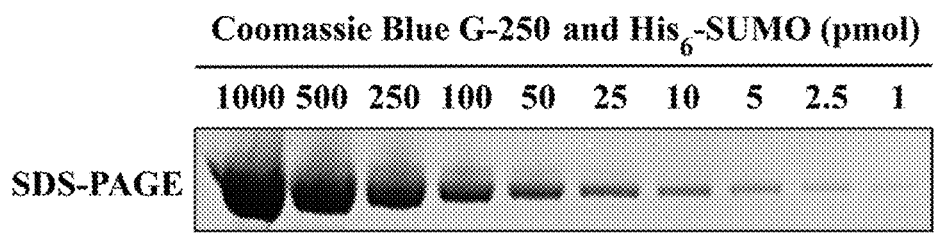
Figure 4C:
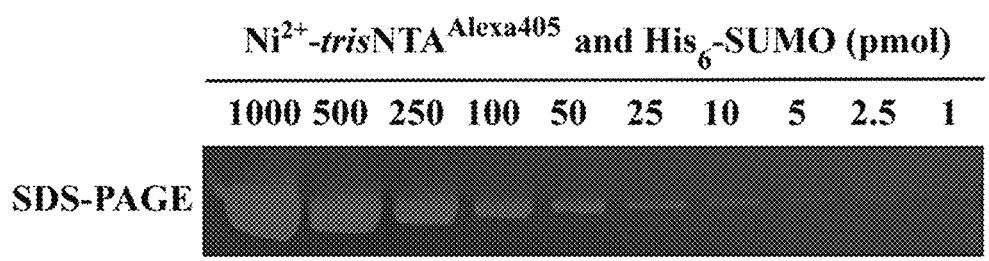
Figure 4D:
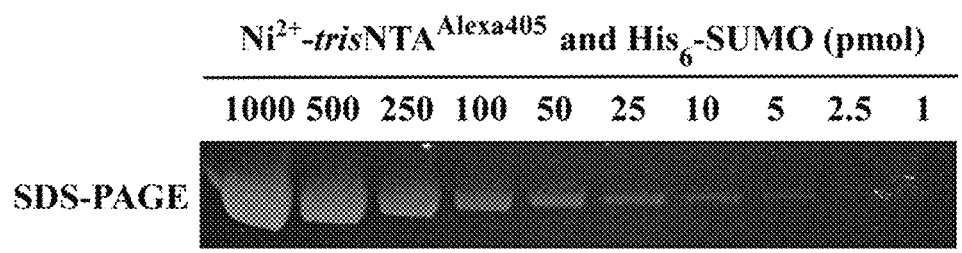
Figure 4E:
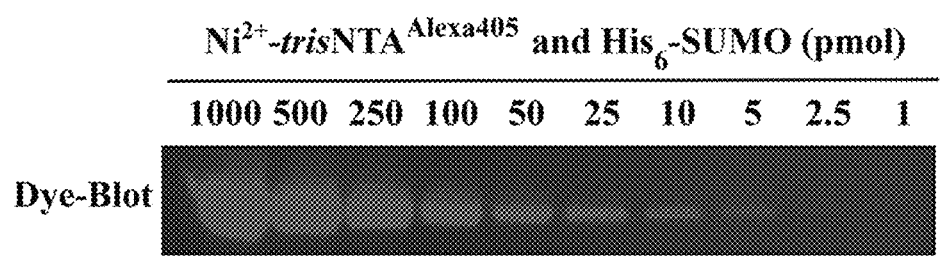
Figure 4F:
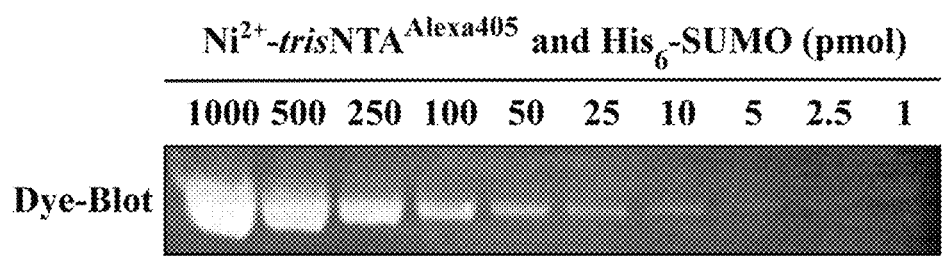

For the staining step, both the gel and the membrane were treated identically. Fresh PBS solution containing 2 μM $Ni^{2+}$-trisNTA$^{Alexa405}$ was prepared and the gel and membrane were submerged in this solution and incubated for 1 hr in the dark with gentle shaking. After one hour, the gel was rinsed with warm water and the membrane was rinsed with 1×TBST and exposed to UV transilluminator equipped with a protective screen. To capture an image as similar as possible to the one available to the naked human eye, both the gel and the membrane were photographed with a regular phone photo camera in the dark (FIGS. 4C,4E). For accuracy, images were also taken with the incorporated camera of the FluorChem Q Image analysis system (FIGS. 4D,4F).

Figure 4G:
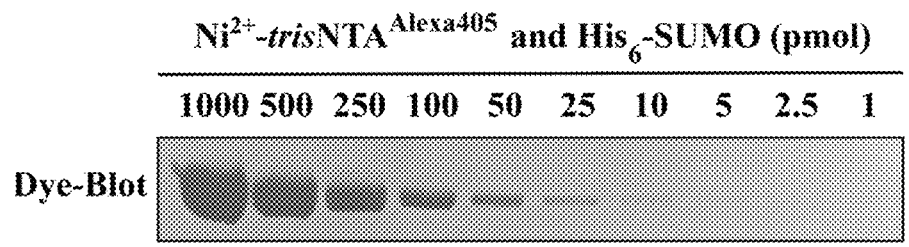

With this simple approach, a limit of ~5 pmol for gel and ~2.5 pmol for membrane were visible to the naked human eye through the protective screen of the transilluminator (FIGS. 4C, 4E). These detection limits were also confirmed by the camera of the FluorChem Q Image analysis system (FIGS. 4D, 4F). Remarkably, this detection limits were achieved without the requirement of any additional time-consuming destaining steps despite the relatively low brightness of $Ni^{2+}$-trisNTA$^{Alexa405}$ (FIG. 2C). Additionally, the membrane could be visualized by using the UV transilluminator and the naked human eye, even under ambient light conditions (FIG. 4G). Moreover, at the end of visualization, the gel can be stained with Coomassie Brilliant Blue (CBB) for complementarity (FIGS. 4A, B). In its G-250 form and by using the fast staining protocol described in the Methods section, CBB allowed the visualization of ~ 1 pmol of $His_6$-SUMO. In the case of the blot membrane, washing in the presence of at least 50 mM EDTA gets rid of the bound $Ni^{2+}$-trisNTA$^{Alexa405}$ and reuse the membrane for future experiments (data not shown).

Figure 2A:
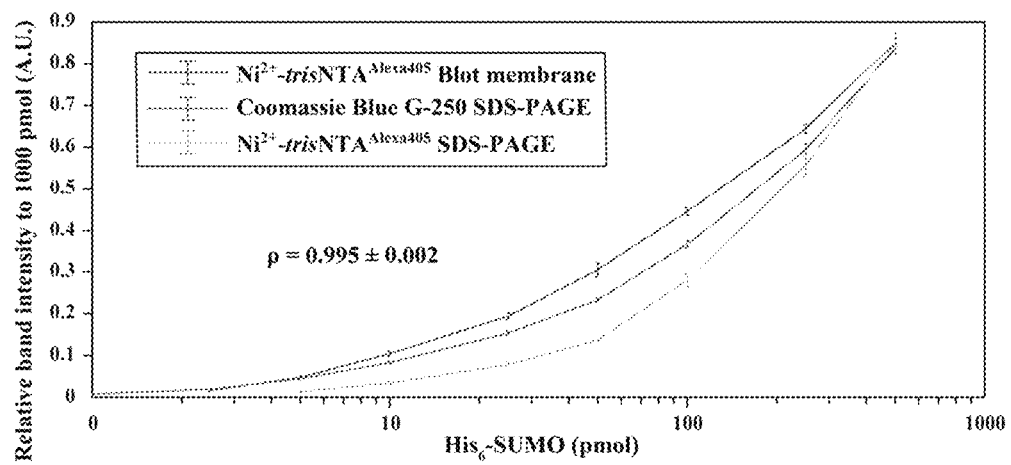
FIG. 2A is a Plot of the normalized band intensities detected by $Ni^{2+}$-trisNTA$^{Alexa405}$, in both SDS-PAGE and blot membrane, and by Coomassie Blue G-250 (CBB) staining, in SDS-PAGE, from the images presented in FIG. 4A-G. The intensity of each band was normalized to the intensity of the 1000 pmol band within the same gel. The correlation coefficient between the $Ni^{2+}$-trisNTA$^{Alexa405}$ and CBB staining in SDS-SPAGE is indicated on the graph together with its 95% confidence interval. Each data point is represented by the average and standard deviation of three independent quantifications using the built-in option of the Image-J software.
Figure 2B:
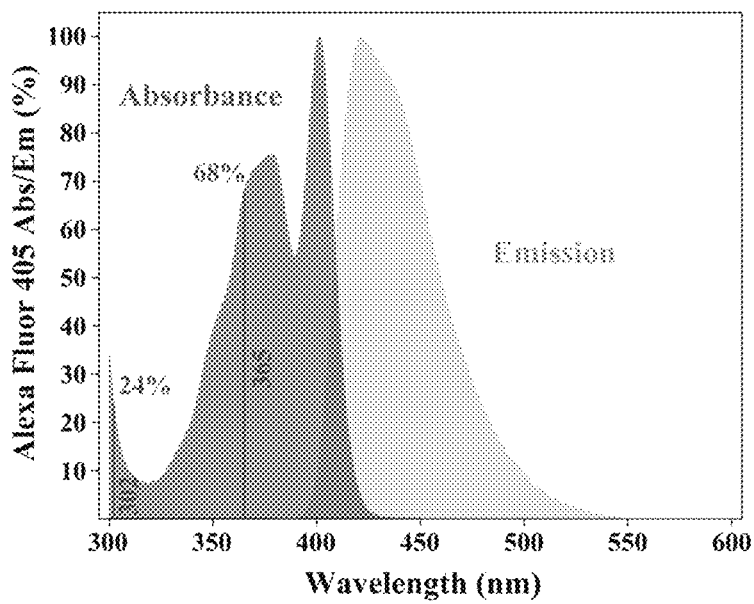
FIG. 2B shows the absorption and emission spectra of Alexa Fluor 405 NHS ester as per the manufacturer's description. The red vertical bars represent the relative absorbance (%) of Alexa Fluor 405 at the indicated wavelength as compared to the maximum of absorbance.
Figure 2C:
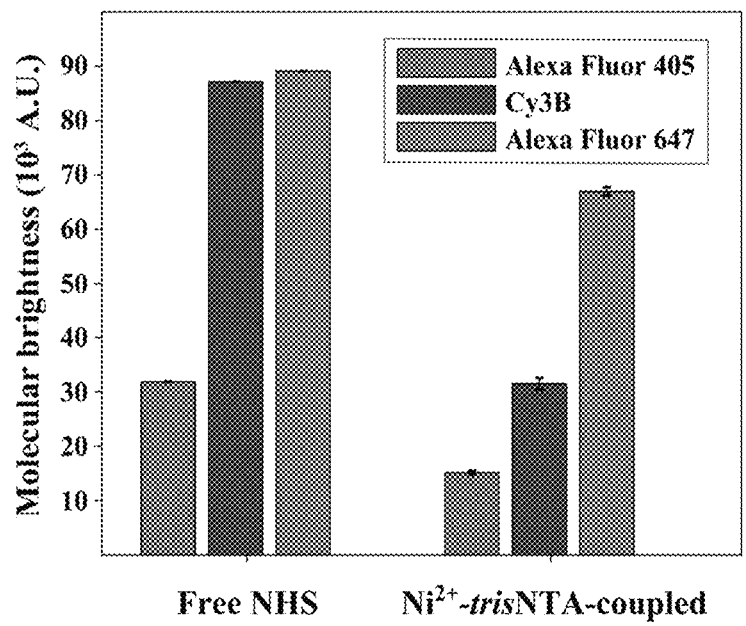
FIG. 2C is a bar chart of the brightness of Alexa Fluor 405, Cy3B and Alexa Fluor 647 as free NHS esters (left set of bars) and $Ni^{2+}$-trisNTA conjugates (right set of bars).

To quantitatively assess the correlation between the CBB and $Ni^{2+}$-trisNTA$^{Alexa405}$ detection, the band intensities in gels and membrane were measured using the built-in function of the ImageJ software and normalized these values to the 1000 pmol band (FIG. 2A). The intensities detected by $Ni^{2+}$-trisNTA$^{Alexa405}$ in both gel and membrane scaled very accurately with the CBB intensities in gel, with a correlation coefficient higher than 99%. From the practical point of view, this high correlation indicates a very good complementarity of $Ni^{2+}$-trisNTA$^{Alexa405}$ and CBB staining within the given detection range of 2.5-500 pmol.

In complex mixture samples, especially in whole cellular extracts, a variety of proteins can show different affinity towards His-tag-binding reagents such as anti-His antibodies as well as metal ion-loaded chelator heads[18-22].

TABLE 1

Photophysical parameters describing the brightness of the $Ni^{2+}$-trisNTA fluorophores conjugates.

| | | | Free NHS ester form | | $Ni^{2+}$-trisNTA-coupled form | | |
|---|---|---|---|---|---|---|---|
| Fluorophore | Maximum absorption (nm) | Extinction coefficient ($M^{-1}cm^{-1}$) | Lifetime (ns) | QY | Brightness (A.U.) | Lifetime (ns) | Brightness (A.U.) | Quenching (%) |
| Alexa Fluor 405 | 401 [a] | 35000 [a] | 3.8 [b, 31] | 0.91 [c] | 31850 | 1.81 ± 0.04 [e] | 15162 ± 340 | 52.4 |
| Cy3B | 559 [a] | 130000 [a] | 2.4 [d, 25] | 0.67 [d, 32] | 87100 | 0.87 ± 0.03 [e] | 31500 ± 1055 | 63.8 |
| Alexa Fluor 647 | 651 [a] | 270000 [a] | 1.0 [a] | 0.33 [a] | 89100 | 0.75 ± 0.01[e] | 66959 ± 780 | 24.9 |

All estimated parameters are derived according to the information described in Methods.
All values have their source indicated as:
[a] as per manufacturer's description,
[b] as approximated by the value of the highly similar Cascade Blue dye as per the adjacent reference,
[c] as approximated by the value of the highly similar iFluor 405 dye as per manufacturer's description,
[d] as described in the adjacent reference and [e] as experimentally determined in the current study.

Figure 5A:
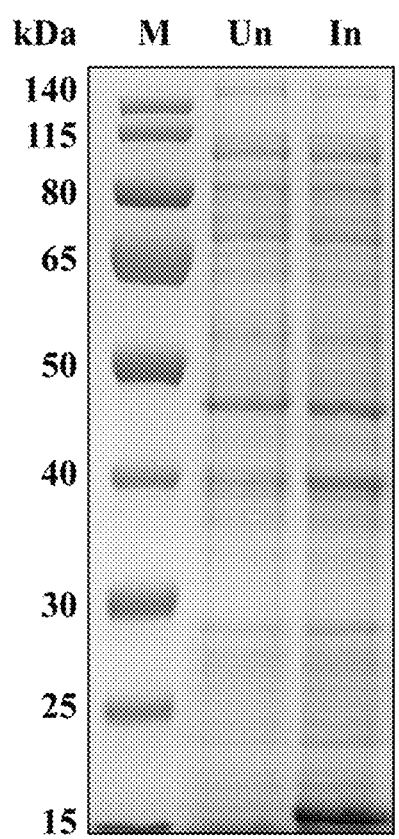
FIGS. 5A-5C show the specificity of $Ni^{2+}$-trisNTA$^{Alexa405}$ in the UVHis-PAGE protocol and comparison with anti-His antibody-based immunoblotting. Uninduced (Un) and induced (In) samples of *E. coli* culture expressing $His_6$-SUMO were run on SDS-PAGE and stained with CBB. The molecular weight marker (M) is PageRuler Prestained Protein Ladder (Thermo Fisher Scientific, 26616) (FIG. 5A). An additional copy of this SDS-PAGE was used for immunoblotting using anti-His antibody. The molecular weight marker (M) is MagicMark XP Western Protein Standard (Thermo Fisher Scientific, LC5603) (FIG. 5B). Prior to CBB staining, the SDS-PAGE gel was stained with $Ni^{2+}$-trisNTA$^{Alexa405}$, illuminated by a UV transilluminator and imaged in the dark (FIG. 5C) with a regular phone photo camera (right) and gel-dock camera (left).
Figure 5B:
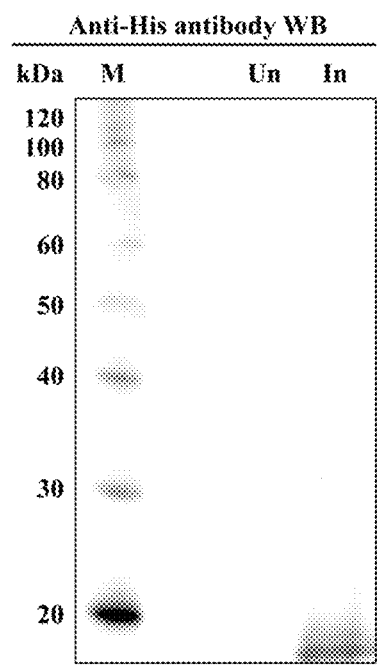
Figure 5C:
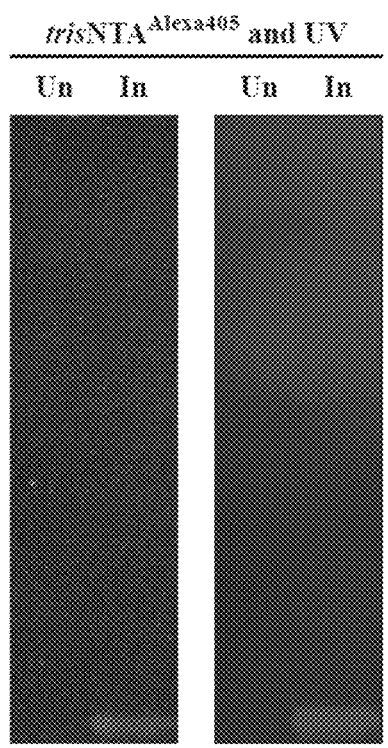

Therefore, the specificity of $Ni^{2+}$-trisNTA$^{Alexa405}$ in the UVHis-PAGE approach was investigated. For detecting $His_6$-SUMO in *E. coli* extract; uninduced and induced samples were prepared as double loading volume (30 μl) and then split into two independent gels. One copy of the gel was transferred to PVDF membrane and blocked with BSA for 1 hr and immunoblotted for 2 hr with anti-His antibody (FIG. 5B). The second copy of the gel was fixed using the fast protocol (12 min). The gel was then stained with $Ni^{2+}$-trisNTA$^{Alexa405}$ as described above and imaged with the regular phone photo camera and with the camera of the FluorChem Q Image analysis system (FIG. 5C). After imaging, the same gel was stained with CBB as previously described (FIG. 5A). A clear additional band at ~15 kDa is visible in the induced as compared to the uninduced sample, corresponding to $His_6$-SUMO. The presence of the His-tag was directly confirmed by the antibody-based immunoblotting (FIG. 5B). $Ni^{2+}$-trisNTA$^{Alexa405}$ signal was highly specific to the confirmed His$_6$-SUMO band under both imaging methods. Notably, no additional unspecific band could be detected either by naked human eye or the camera of the analysis system. These experiments clearly illustrate the high specificity of detection of the Ni$^{2+}$-trisNTA$^{Alexa405}$ in the UVHis-PAGE approach, even in complex mixture samples.

Discussion

The current studies describe UVHis-PAGE, a method for detection of His-tagged proteins that bypasses the need for antibody-based immunoblotting. The method allows for the visualization of as low as 5 pmol for SDS-PAGE or 2.5 pmol in blot membrane of His$_6$-tagged protein while using a simple UV transilluminator as excitation source and the naked human eye for visualization. The method includes a metal ion-loaded NTA-based chelator head conjugated to a UV-excitable fluorophore with visible emission.

monoNTA[3,4] and trisNTA[5-9] represent two popular commercially available chelator heads containing a primary amine that can be directly used for coupling to NHS ester fluorophores. Ni$^{2+}$-trisNTA has been previously optimized to enhance its binding affinity to His$_6$-tags by 1000-folds as compared to Ni$^{2+}$-monoNTA[8]. Therefore, our first set of experiments was designed to directly evaluate the performance of these two chelator heads in SDS-PAGE detection of His$_6$-taged proteins. A complete lack of detection was previously shown when Ni$^{2+}$-trisNTA was employed in a pre-run staining protocol[17]. With Ni$^{2+}$-hexaNTA being the only known chelator head that can withstand the harsh conditions of the pre-run staining protocol 17, we switched to a post-run staining protocol (FIG. 1A) in order to directly compare monoNTA and trisNTA.

In comparison to Ni$^{2+}$-monoNTA, Ni$^{2+}$-trisNTA resulted in ~25-fold increase in the detection limit of His$_6$-SUMO (FIGS. 3A-3D). In fact, as per the manufacturer's description, the Atto dyes, that were attached to Ni$^{2+}$-monoNTA, are brighter than their Alexa or Cyanine counterparts, that were attached to Ni$^{2+}$-trisNTA, which makes this result even more outstanding. On a theoretical level, these results also show that in complex environments, such as in and out of gel diffusion, a difference in the affinity constant of number of folds is not necessary directly translated into the same number of folds in relation to the difference in the detection limit. Nevertheless, given this considerable enhancement, trisNTA was chosen for the subsequent experiments.

The detection limit of Ni$^{2+}$-trisNTA$^{Alexa647}$ of ~0.1 pmol in post-run staining conditions is similar to that of Ni$^{2+}$-hexaNTA$^{Alexa647}$ (~0.2 µmol) in pre-run staining conditions[17]. This similarity opens two directions for further investigation. First, it is possible that this detection limit is imposed by the conjugated fluorophore itself rather than by the chelator head; a case in which brighter small organic fluorophores should be developed and coupled to these chelator heads to enhance their detection limits. This possibility is sustained also by directly comparing the detection limit of Ni$^{2+}$-trisNTA$^{Alexa647}$ (FIG. 3D) with Ni$^{2+}$-trisNTA$^{Alexa405}$ (FIG. 4C), which despite using the same chelator head, resulted in around ~25-fold difference in favor of the brighter Alexa Fluor 647 and the more advanced equipment used for its visualization (FIG. 2C and Table 1). Alternatively, since Ni$^{2+}$-hexaNTA is ~1000-fold stronger binder than trisNTA[16] but resulted in a similar detection limit, it is possible that any chelator head may not be used at its maximum capacity under SDS-PAGE pre-run staining conditions. This possibility is also sustained by the completely different behavior of Ni$^{2+}$-trisNTA$^{Alexa647}$ under post-run staining conditions in the current study and under pre-run staining conditions previously described[17]. Accordingly, it is expected that subjecting hexaNTA or any other chelator head to similar post-run staining as disclosed here for trisNTA$^{Alexa647}$, should improve its detection limit, when compared to pre-run staining.

Apart from the theoretical advantage of being able to directly compare the staining kinetics by different fluorophore-coupled chelator heads, post-run staining conditions offer several advantages, but also a drawback as compared to pre-run staining conditions. Since trisNTA can be employed, it allows the detection of the most common form His$_6$-tag. Second, as the complex is formed post-run, it does not induce an undesired upper shift in the apparent molecular weight of the protein of interest. Lastly, it allows for gel fixation and later staining without the requirement of immediate imaging. As a drawback, it consumes larger amounts of Ni$^{2+}$-trisNTA conjugates in the staining step. Nevertheless, both protocols perform similarly well, with a detection limit similar to that of antibody-based immunoblotting.

Subsequent studies focused on reducing the ease of detection, by changing the fluorophore to Alexa Fluor 405. This dye is UV-excitable and exhibits fluorescence emission in the visible part of the spectrum (FIG. 2B). Typical detection usually employed green or red fluorophores, which require specialized excitation sources and detection systems. Through coupling of Alexa Fluor 405 to Ni$^{2+}$-trisNTA, we were able to detect as low as 5 pmol for SDS-PAGE or 2.5 pmol in blot membrane of His$_6$-SUMO, by using a simple UV transilluminator as excitation source and the naked human eye as detector. This detection showed excellent correlation with that of CBB staining (FIG. 4A-4G and FIG. 3A-3D) and was highly specific to the His-tagged protein even in complex mixture samples (FIG. 5A-5C). These results are particularly outstanding especially in the context of the reduced brightness of UV-excitable dyes such as Alexa Fluor 405, as well as their heavy quenching upon conjugation to Ni$^{2+}$-trisNTA (FIG. 2C and Table 1). Therefore, in the future, such simplified UV-based detection systems could gain a significant improvement from the development of brighter small organic fluorophores with considerable UV excitation and visible emission.

In conclusion, UVHis-PAGE can be an ideal tool for simple and rapid detection of His-tagged proteins in applications where specialized fluorescence detection is unavailable and traditional antibody-based immunoblotting is too costly or time consuming. Apart from indicating the presence of a certain epitope, immunoblotting with secondary antibodies, based on both chemiluminescent and fluorescent detection, has been used as a quantitative tool to determine the epitope amount. We envision that for a given set of conditions (such as gel percentage and composition or blot membrane composition, type and concentration of Ni$^{2+}$-MCH conjugate used, staining and destaining times and imaging parameters), the currently described methods can also be used as quantitative tools, mainly through the use of a calibration curve similar to the dependence described in FIG. 2A. For all the currently presented methods, all the necessary chemical components are commercially available and through the use of the well-established amine-NHS chemistry require minimum conditions for efficient coupling. In the broader sense, the current work also points to the benefits of usage of UV-excitable dyes in various assays, which despite their lower brightness can offer a simple platform for detection due to the simplified equipment requirements.

REFERENCES

1. Young, C. L., Britton, Z. T. & Robinson, A. S. Recombinant protein expression and purification: a comprehensive review of affinity tags and microbial applications. *Biotechnol J* 7, 620-634, doi: 10.1002/biot.201100155 (2012).
2. Bornhorst, J. A. & Falke, J. J. Purification of proteins using polyhistidine affinity tags. *Methods Enzymol* 326, 245-254, doi: 10.1016/s0076-6879 (00) 26058-8 (2000).
3. Guignet, E. G., Hovius, R. & Vogel, H. Reversible site-selective labeling of membrane proteins in live cells. *Nat Biotechnol* 22, 440-444, doi: 10.1038/nbt954 (2004).
4. Lai, Y. T. et al. Rapid labeling of intracellular His-tagged proteins in living cells. *Proc Natl Acad Sci USA* 112, 2948-2953, doi: 10.1073/pnas.1419598112 (2015).
5. Huang, Z., Hwang, P., Watson, D. S., Cao, L. & Szoka, F. C., Jr. Tris-nitrilotriacetic acids of subnanomolar affinity toward hexahistidine tagged molecules. *Bioconjug Chem* 20, 1667-1672, doi: 10.1021/bc900309n (2009).
6. Huang, Z., Park, J. I., Watson, D. S., Hwang, P. & Szoka, F. C., Jr. Facile synthesis of multivalent nitrilotriacetic acid (NTA) and NTA conjugates for analytical and drug delivery applications. *Bioconjug Chem* 17, 1592-1600, doi: 10.1021/bc0602228 (2006).
7. van Broekhoven, C. L. & Altin, J. G. The novel chelator lipid 3 (nitrilotriacetic acid)-ditetradecylamine (NTA(3)-DTDA) promotes stable binding of His-tagged proteins to liposomal membranes: potent anti-tumor responses induced by simultaneously targeting antigen, cytokine and costimulatory signals to T cells. *Biochim Biophys Acta* 1716, 104-116, doi: 10.1016/j.bbamem.2005.09.003 (2005).
8. Lata, S., Reichel, A., Brock, R., Tampe, R. & Piehler, J. High-affinity adaptors for switchable recognition of histidine-tagged proteins. *Journal of the American Chemical Society* 127, 10205-10215, doi: 10.1021/ja050690c (2005).
9. Gatterdam, K., Joest, E. F., Gatterdam, V. & Tampe, R. The Scaffold Design of Trivalent Chelator Heads Dictates Affinity and Stability for Labeling His-tagged Proteins in vitro and in Cells. *Angewandte Chemie (International ed. in English)* 57, 12395-12399, doi: 10.1002/anie.201802746 (2018).
10. Bartoschik, T. et al. Near-native, site-specific and purification-free protein labeling for quantitative protein interaction analysis by MicroScale Thermophoresis. *Sci Rep* 8, 4977, doi: 10.1038/s41598-018-23154-3 (2018).
11. Braner, M., Kollmannsperger, A., Wieneke, R. & Tampe, R. 'Traceless' tracing of proteins-high-affinity trans-splicing directed by a minimal interaction pair. *Chem Sci* 7, 2646-2652, doi: 10.1039/c5sc02936h (2016).
12. Wieneke, R. & Tampe, R. Multivalent Chelators for In Vivo Protein Labeling. *Angewandte Chemie (International ed. in English)* 58, 8278-8290, doi: 10.1002/anie.201811293 (2019).
13. Lata, S. & Piehler, J. Stable and functional immobilization of histidine-tagged proteins via multivalent chelator headgroups on a molecular poly(ethylene glycol) brush. *Anal Chem* 77, 1096-1105, doi: 10.1021/ac048813j (2005).
14. Lata, S., Gavutis, M., Tampe, R. & Piehler, J. Specific and stable fluorescence labeling of histidine-tagged proteins for dissecting multi-protein complex formation. *Journal of the American Chemical Society* 128, 2365-2372, doi: 10.1021/ja0563105 (2006).
15. Valiokas, R. et al. Self-assembled monolayers containing terminal mono-, bis-, and tris-nitrilotriacetic acid groups: characterization and application. *Langmuir* 24, 4959-4967, doi: 10.1021/la703709a (2008).
16. Gatterdam, K., Joest, E. F., Dietz, M. S., Heilemann, M. & Tampe, R. Super-Chelators for Advanced Protein Labeling in Living Cells. *Angewandte Chemie (International ed. in English)* 57, 5620-5625, doi: 10.1002/anie.201800827 (2018).
17. Bruchert, S., Joest, E. F., Gatterdam, K. & Tampe, R. Ultrafast in-gel detection by fluorescent super-chelator probes with HisQuick-PAGE. *Commun Biol* 3, 138, doi: 10.1038/s42003-020-0852-1 (2020).
18. Andersen, K. R., Leksa, N. C. & Schwartz, T. U. Optimized *E. coli* expression strain LOBSTR eliminates common contaminants from His-tag purification. *Proteins* 81, 1857-1861, doi: 10.1002/prot.24364 (2013).
19. Wulfing, C., Lombardero, J. & Pluckthun, A. An *Escherichia coli* protein consisting of a domain homologous to FK506-binding proteins (FKBP) and a new metal binding motif. *J Biol Chem* 269, 2895-2901 (1994).
20. Bolanos-Garcia, V. M. & Davies, O. R. Structural analysis and classification of native proteins from *E. coli* commonly co-purified by immobilised metal affinity chromatography. *Biochim Biophys Acta* 1760, 1304-1313, doi: 10.1016/j.bbagen.2006.03.027 (2006).
21. Williams, G. J., Breazeale, S. D., Raetz, C. R. & Naismith, J. H. Structure and function of both domains of ArnA, a dual function decarboxylase and a formyltransferase, involved in 4-amino-4-deoxy-L-arabinose biosynthesis. *J Biol Chem* 280, 23000-23008, doi: 10.1074/jbc.M501534200 (2005).
22. Roof, W. D., Horne, S. M., Young, K. D. & Young, R. slyD, a host gene required for phi X174 lysis, is related to the FK506-binding protein family of peptidyl-prolyl cis-trans-isomerases. *J Biol Chem* 269, 2902-2910 (1994).
23. Piatkevich, K. D. & Verkhusha, V. V. Guide to red fluorescent proteins and biosensors for flow cytometry. *Methods Cell Biol* 102, 431-461, doi: 10.1016/B978-O-12-374912-3.00017-1 (2011).
24. Holmes, A. S., Suhling, K. & Birch, D. J. Fluorescence quenching by metal ions in lipid bilayers. *Biophys Chem* 48, 193-204, doi: 10.1016/0301-4622 (93) 85010-f (1993).
25. Rashid, F. et al. Initial state of DNA-Dye complex sets the stage for protein induced fluorescence modulation. *Nat Commun* 10, 2104, doi: 10.1038/s41467-019-10137-9 (2019).
26. Raducanu, V. S. et al. A direct fluorescent signal transducer embedded in a DNA aptamer paves the way for versatile metal-ion detection. *Sensor Actuat B-Chem* 304, doi: ARTN 127376 10.1016/j.snb.2019.127376 (2020).
27. Grushka, E. Characterization of exponentially modified Gaussian peaks in chromatography. *Anal Chem* 44, 1733-1738, doi: 10.1021/ac60319a011 (1972).
28. Kalambet, Y., Kozmin, Y., Mikhailova, K., Nagaev, I. & Tikhonov, P. Reconstruction of chromatographic peaks using the exponentially modified Gaussian function. *J Chemometr* 25, 352-356, doi: 10.1002/cem.1343 (2011).
29. Tehseen, M. et al. Proliferating cell nuclear antigen-agarose column: A tag-free and tagdependent tool for protein purification affinity chromatography. *J Chromatogr A*, doi: 10.1016/j.chroma.2019.06.008 (2019).
30. Raducanu, V. S., Tehseen, M., Shirbini, A., Raducanu, D. V. & Hamdan, S. M. Twochromatographic schemes for protein purification involving the biotin/avidin interaction under native conditions. *J Chromatogr A*, 461051, doi: 10.1016/j.chroma.2020.461051 (2020).
31 Taylor, R. M., Riesselman, M. H., Lord, C. I., Gripentrog, J. M. & Jesaitis, A. J. Anionic lipid-induced conformational changes in human phagocyte flavocytochrome b precede assembly and activation of the NADPH oxidase complex. *Arch Biochem Biophys* 521, 24-31, doi: 10.1016/j.abb.2012.01.018 (2012).
32 Cooper, M. et al. Cy3B: improving the performance of cyanine dyes.

We claim:

1. A method for detecting His-tagged proteins using metal ion-chelating nitrilotriacetate (NTA)-based probes and polyacrylamide gel electrophoresis (PAGE), comprising:
   (a) contacting the His-tagged proteins with a metal ion-loaded and fluorescently labeled NTA probe, the method comprising contacting a polyacrylamide gel or western blot membrane, following separation by PAGE, with a composition comprising an effective amount of metal ion-loaded NTA probes, for an effective amount of time to allow binding of the probe to His-tagged proteins on the gel; and
   (b) detecting the probes (and therefore the His-tagged proteins) by exposing the gel or western blot membrane to a UV-light source,
   wherein the metal ion-loaded NTA probes are each coupled to a UV-excitable fluorophore with visible emission, and
   wherein the method comprises transferring His-tagged proteins separated by PAGE onto a western blot membrane prior to contacting the western blot membrane with the NTA probes.

2. The method of claim 1, wherein the metal ion is selected from the group consisting of $Ni^{2+}$, $Zn^{2+}$, $Cu^{2+}$, $Cd^{2+}$, $Hg^{2+}$, $Co^{2+}$ and $Fe^{2+}$.

3. The method of claim 1, wherein the PAGE is sodium dodecyl sulfate (SDS)-PAGE.

4. The method of claim 1, wherein after PAGE, the proteins are fixed in the gels by contacting the gel with 1× fixation solution with or without heating.

5. The method of claim 4, wherein the gel is fixed with a 1× fixation solution consisting of 40% methanol, 20% glacial acetic acid and 40% water and the gel is cleaned with water while heating.

6. The method of claim 1, wherein the western blot membrane is polyvinylidene fluoride or nitrocellulose.

7. The method of claim 1, wherein (a) the metal ion is $Ni^{2+}$, and/or (b) the metal ion $Ni^{2+}$ NTA probe is coupled with a UV-excitable fluorophore with visible emission.

8. The method of claim 1, comprising detecting the presence of His-tagged proteins using a UV transilluminator wherein the presence of the His-tagged proteins is detected by visualizing bands with the expected molecular weights on the gel.

9. The method of claim 8, comprising a UV transilluminator as an excitation source and the human eye or a bench camera for visualization.

10. The method of claim 9, comprising detecting the His-tagged proteins using a UV transilluminator.

11. A method for detecting His-tagged proteins using metal ion-chelating nitrilotriacetate (NTA)-based probes and polyacrylamide gel electrophoresis (PAGE), comprising,
   (a) contacting the His-tagged proteins with metal ion-loaded and fluorescently labeled NTA probes and
   (b) detecting the probe (and therefore the His-tagged proteins),
   wherein the NTA probe are each coupled to a fluorophore with the majority of emission and excitation in the visible region of the electromagnetic spectrum,
   wherein the method comprises contacting a polyacrylamide gel or western blot membrane following PAGE with a composition comprising an effective amount of the metal ion-loaded NTA probes each coupled to a fluorophore for an effective amount of time to allow binding of the probes to the His-tagged proteins, and detecting the presence of the probes (and therefore of the His-tagged proteins),
   wherein the method further comprises transferring His-tagged proteins separated by PAGE onto a western blot membrane prior to contacting the western blot membrane with the NTA probes.

12. The method of claim 11, wherein the His-tagged proteins are not contacted with the probe prior to subjecting the samples to PAGE, and wherein the probe is not subjected to PAGE.

13. The method of claim 1, wherein: (a) the NTA probe comprises a multivalent NTA moiety; and/or (b) the PAGE does not include a loading dye.

14. The method of claim 1, wherein the multivalent NTA moiety is bisNTA, trisNTA, tetrakisNTA or hexaNTA (hexavalent N-nitriloacetic acid).

15. The method of claim 1, comprising one or more washing steps following contacting His-tagged protein-containing gel with the composition comprising the metal ion-loaded NTA probe coupled to the fluorophore.

16. The method of claim 15, comprising washing the gel for at least 10 minutes, to remove unbound metal ion-loaded NTA probe coupled to the fluorophore.

17. The method of claim 16, comprising washing the gel for about 30 minutes, and detecting the His-tagged proteins.

18. The method of claim 13 wherein: (a) the NTA probe comprises a multivalent NTA moiety; and (b) the PAGE does not include a loading dye.

* * * * *